US009389235B2

(12) United States Patent
Weinschenk et al.

(10) Patent No.: US 9,389,235 B2
(45) Date of Patent: Jul. 12, 2016

(54) METHODS OF USING BIOMARKERS FOR PREDICTING THE OUTCOME OF AN IMMUNOTHERAPY AGAINST CANCER

(71) Applicant: IMMATICS BIOTECHNOLOGIES GMBH, Tuebingen (DE)

(72) Inventors: Toni Weinschenk, Aichwald (DE); Harpreet Singh, Tuebingen (DE); Andrea Mahr, Tuebingen (DE); Jens Fritsche, Tuebingen (DE)

(73) Assignee: IMMATICS BIOTECHNOLOGIES GMBH, Tuebingen (DE)

( * ) Notice: Subject to any disclaimer, the term of this patent is extended or adjusted under 35 U.S.C. 154(b) by 238 days.

(21) Appl. No.: 14/158,054

(22) Filed: Jan. 17, 2014

(65) Prior Publication Data

US 2014/0234347 A1    Aug. 21, 2014

(30) Foreign Application Priority Data

Dec. 15, 2010    (GB) .................................. 1021289.2

(51) Int. Cl.
  *G01N 33/53*   (2006.01)
  *G01N 33/567*  (2006.01)
  *G01N 33/574*  (2006.01)
  *G01N 33/50*   (2006.01)

(52) U.S. Cl.
  CPC ...... *G01N 33/57488* (2013.01); *G01N 33/5011* (2013.01); *G01N 33/574* (2013.01); *G01N 2333/523* (2013.01); *G01N 2333/775* (2013.01); *G01N 2800/52* (2013.01)

(58) Field of Classification Search
  CPC ........................ G01N 33/574; G01N 33/57488
  See application file for complete search history.

(56) References Cited

FOREIGN PATENT DOCUMENTS

| EP | 1 777 523   | 4/2007 |
| EP | 2105740     | 9/2009 |
| WO | 2010/003773 | 1/2010 |
| WO | 2010/076322 | 7/2010 |

OTHER PUBLICATIONS

Riesen; WF; Fettstoffwechsel, Referenzbereich. In Labor and Diagnose, L. Thomas, ed. (Frankfurt/Main: TH—Books Verlagsgesellschaft mbH); 2008; p. 225-248.
Shimada et al.; "Both TH2 and TH1 Chemokines (TARC/CCL17, MDC/CCL22, and MIGICXCL9) Are Elevated in Sera From Patients With Atopic Dermatitis"; Journal of Dermatological Science (2004) 34; pp. 201-208; Elsevier Ireland LTD.
Echigo et al., "Both Th1 and Th2 chemokines are elevated in sera of patients with autoimmune blistering diseases", Arch. Dermatol. Res, Published online Apr. 1, 2006, vol. 298, pp. 38-45, Springer-Verlag 2006.
Fujii et al., "Serum levels of a Th1 chemoattractant IP-10 and Th2 chemoattractants, TARC and MDC, are elevated in patients with systemic sclerosis", Journal of Dermatological Science, Jun. 2004, vol. 35, No. 1, pp. 43-51, Published by Elsevier Ireland Ltd.
Leung et al., "Serum concentration of macrophage-derived chemokine may be a useful inflammatory marker for assessing severity of atopic dermatitis in infants and young children", Pediatric Allergy Immunology, Jan. 19, 2003, vol. 14, pp. 296-301, 2003 Blackwell Munksgaard.
Moroni et al., "Eosinophils and C4 predict clinical failure of combination immunotherapy with very low dose subcutaneous interleukin-2 and interferon in renal cell carcinoma patients", Haematologica, Mar. 2000, vol. 85, No. 3, pp. 298-303.
Muller et al., "Chronic inflammation that facilitates tumor progression creates local immune suppression by inducing indoleamine 2,3 dioxygenase", Proc Natl. Acad. Sci. U. S. A., Nov. 4, 2008, vol. 105, No. 44, pp. 17073-17078, The National Academy of Sciences of the USA.
Panse et al., "Chemokine CXCL13 is overexpressed in the tumour tissue and in the peripheral blood of breast cancer patients", British Journal of Cancer, Jul. 2008, Cancer Research UK, vol. 99, pp. 930-938.
Rashid et al., "A pre-operative elevated neutrophil: lymphocyte ratio does not predict survival from oesophageal cancer resection", World Journal of Surgical Oncology, Jan. 6, 2010, vol. 8, No. 1, pp. 1-10.
Saeki et al., "Thymus and activation regulated chemokine (TARC)/CCL17 and skin diseases", Journal of Dermatological Science, Aug. 2006 Published by Elsevier Ireland Ltd., vol. 43, Issue No. 2, pp. 75-84.
Sansonno et al., "Increased serum levels of the chemokine CXCL13 and up-regulation of its gene expression are distinctive features of HCV-related cryoglobulinemia and correlate with active cutaneous vasculitis", Blood, Jun. 12, 2008, vol. 112, pp. 1620-1627, 2011 The American Society of Hematology.
Sasaki et al., "Prognostic value of preoperative peripheral blood monocyte count in patients with hepatocellular carcinoma", Surgery, Jun. 2006, vol. 139, Issue No. 6, pp. 755-764, Mosby, Inc.
Sekiya et al., "Increased levels of a TH2-type CC chemokine thymus and activation-regulated chemokine (TARC) in serum and induced sputum of asthmatics", Allergy, Feb. 2002, vol. 57, Issue No. 2, pp. 173-177, Munksgaard.
Simon et al., "Eosinophilic disorders", Journal of Allergy Clinical Immunology, Jun. 2007, vol. 119, Issue No. 6, pp. 1291-1300, American Academy of Allergy, Asthma & Immunology.
Su et al., "Apolipoprotein A-I (apoA-I) and apoA-I mimetic peptides inhibit tumor development in a mouse model of ovarian cancer", PNAS, vol. 107, No. 46, Nov. 1, 2010, pp. 19997-20002.
Sugawara et al., "TARC in allergic disease" Allergy, Published Sep. 25, 2001, vol. 57, pp. 180-181.

(Continued)

*Primary Examiner* — Prema Mertz
(74) *Attorney, Agent, or Firm* — McBee Moore Woodward Vanik IP, LLC.

(57) ABSTRACT

The present invention relates to methods for predicting the effect of an immunotherapy against cancer in a patient based on new biomarkers. The present invention furthermore relates to a prognosis regarding the outcome based on said biomarkers. The present invention furthermore relates to panels of biomarkers for use in the above methods.

9 Claims, 7 Drawing Sheets

(56) References Cited

OTHER PUBLICATIONS

Vallejo et al., "T-cell senescence: a culprit of immune abnormalities in chronic inflammation and persistent infection", Trends in Molecular Medicine, Mar. 2004, vol. 10, No. 3, pp. 119-124.

Vermaat et al., "Two-protein signature of novel serological markers apolipoprotein-A2 and serum amyloid alpha predicts prognosis in patients with metastatic renal cell cancer and improves the currently used prognostic survival models", Annals of Oncology, vol. 21, pp. 1472-1481, Published online Dec. 19, 2009, Published by Oxford University Press.

Wanner et al., "Serum carnitine levels and carnitine esters of patients after kidney transplantation: role of immunosuppression", Metabolism, Mar. 1988, vol. 37, No. 3, pp. 263-267, Grune & Stratton, Inc.

Longenecker et al., "Immune responses of Mice and human breast cancer patients following immunizaiton with synthetic sialyl-Tn conjugated to KLH plus detox adjuvant", Annals New York Academy of Science, Aug. 12, 1993, vol. 690, pp. 276-291.

Sachan et al., "The Serum Carnitine Status of Cancer Patients", Journal of the American College of Nutrition, vol. 6, No. 2, Apr. 1987, pp. 145-150, John Wiley & Sons, Inc__.

Banchereau et al., "Immune and clinical responses in patients with metastatic melanoma to CD34+ progenitor-derived dendritic cell vaccine", Cancer Research, Sep. 1, 2001, vol. 61, pp. 6451-6458.

Haeryfar et al., "The thymus and the acute phase response", Cellular and Molecular Biology, Feb. 2001, vol. 47, No. 1, pp. 145-156.

Donskov et al., "Impact of Immune parameters on long-term survival in metastatic renal cell carcinoma", Journal of Clinical Oncology, vol. 24, No. 13, May 1, 2006, pp. 1997-2005, American Society of Clinical Oncology.

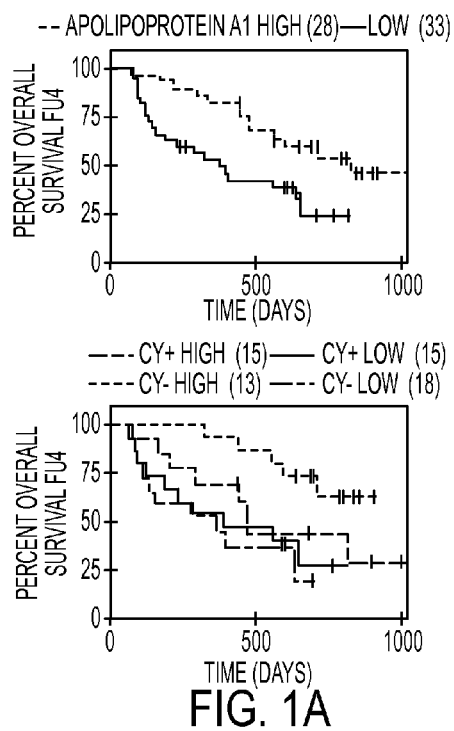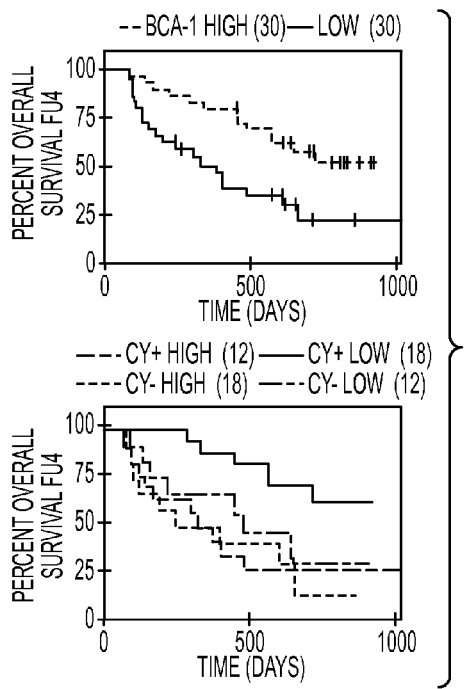
FIG. 1A    FIG. 1B
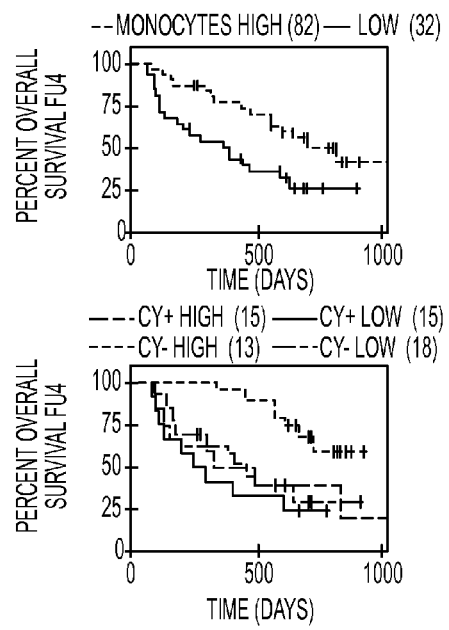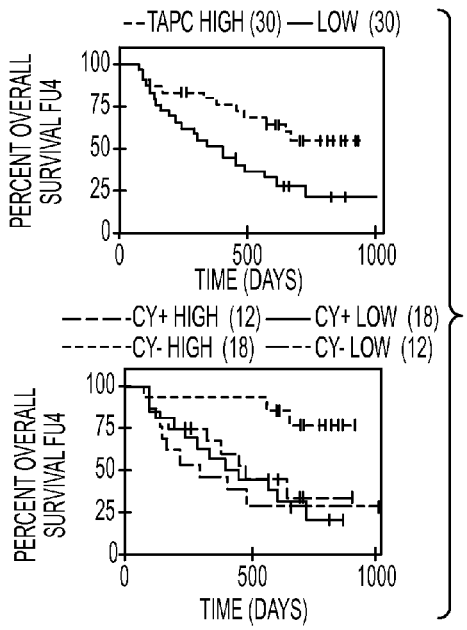
FIG. 1C    FIG. 1D

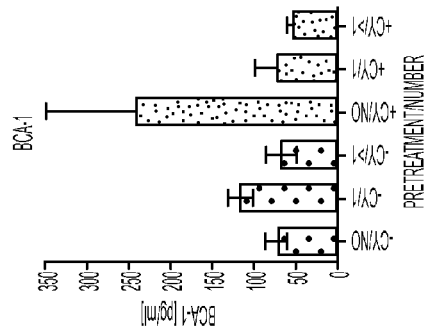

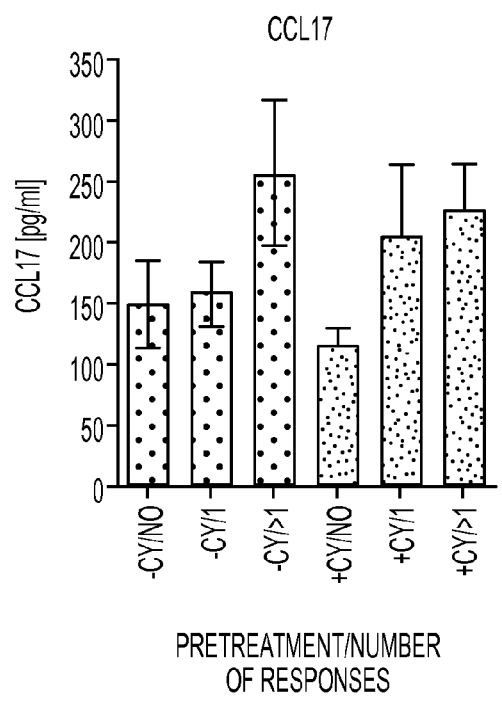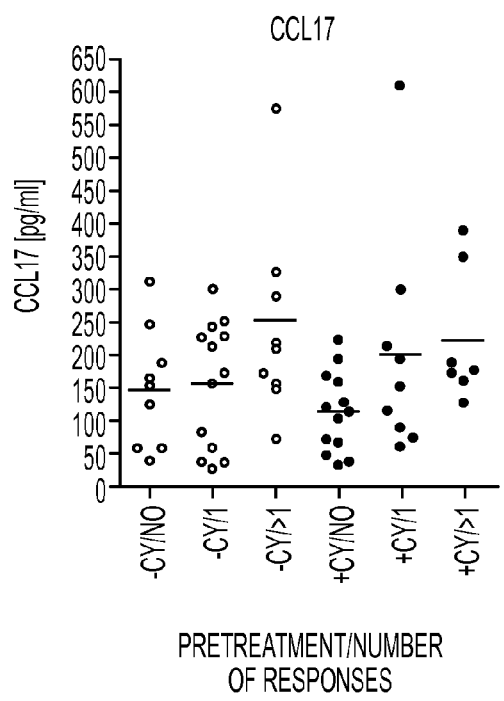
FIG. 2F
FIG. 2G

METHODS OF USING BIOMARKERS FOR PREDICTING THE OUTCOME OF AN IMMUNOTHERAPY AGAINST CANCER

CROSS REFERENCE TO RELATED APPLICATIONS

This application is a continuation of U.S. application Ser. No. 13/302,674, filed Nov. 22, 2011, which claims priority to United Kingdom Application No. 1021289.6, filed Dec. 15, 2010; and the benefit of U.S. Provisional Application No. 61/416,981, filed Nov. 24, 2010; and the benefit of U.S. Provisional Application No. 61/423,652, filed Dec. 16, 2010, the content of all of which are incorporate herein by reference in their entireties. This application includes a sequence listing including 50 sequences. For the purposes of the present invention, all references as cited herein are incorporated by reference in their entireties.

BACKGROUND

A. Field of the Invention

The present invention relates to methods for predicting the effect of an immunotherapy against cancer in a patient based on new biomarkers. The present invention furthermore relates to a prognosis regarding the outcome based on said biomarkers. The present invention furthermore relates to panels of biomarkers for use in the above methods.

B. Brief Description of Related Art

Stimulation of an immune response is dependent upon the presence of antigens recognized as foreign by the host immune system. The discovery of the existence of tumor-associated and tumor-specific antigens has raised the possibility of using a host's immune system to intervene in tumor growth. Various mechanisms of harnessing both the humoral and cellular arms of the immune system are currently being explored for cancer immunotherapy.

Certain elements of the cellular immune response are capable of specifically recognizing and destroying tumor cells. The isolation of cytotoxic T-cells (CTLs) from tumor-infiltrating cell populations or from peripheral blood suggests that these cells play an important role in the natural immune defense against cancer (Cheever et al., Annals N.Y. Acad. Sci. 1993 690:101-112; Zeh H J, Perry-Lalley D, Dudley M E, Rosenberg S A, Yang J C; J. Immunol. 1999, 162(2):989-94). CD8-positive (CD8+) T-cells in particular, which recognize complexes of major histocompatibility complex (MHC) class I molecules and peptides of usually 8 to 10 amino acid residues derived from cytosolic proteins or defective ribosomal products (DRiPs) (Schubert U, Anton L C, Gibbs J, Norbury C C, Yewdell J W, Bennink J R. Nature 2000; 404(6779):770-774), play an important role in this response. Human MHC-molecules are also designated as human leukocyte antigens (HLA).

There are two classes of MHC-molecules: MHC class I molecules can be found on most cells having a nucleus and present peptides that result from proteolytic cleavage of endogenous proteins, DRiPs, and larger peptides. MHC class II molecules can be found predominantly on professional antigen presenting cells (APCs) and present peptides of exogenous proteins that are taken up by APCs, and are subsequently processed (Cresswell P. Annu. Rev. Immunol. 1994; 12:259-93). Complexes of peptide and MHC class I molecules are recognized by CD8+ CTLs bearing the appropriate T cell receptor (TCR), while complexes of peptide and MHC class II molecules are recognized by CD4+ helper-T-cells bearing the appropriate TCR. It is well known that the TCR, the peptide and the MHC are thereby present in a stoichiometric amount of 1:1:1.

For a peptide to elicit a cellular immune response, it must bind to an MHC-molecule. This process depends on the allele of the MHC-molecule and on the amino acid sequence of the peptide. MHC class I-binding peptides are usually 8, 9 or 10 amino acid residues in length and contain conserved residues ("anchors") in their sequences that interact with the corresponding binding groove of the MHC-molecule. Thus, each MHC allele has a "binding motif" determining which peptides can bind specifically to the binding groove (Rammensee H. G., Bachmann J. and Stevanovic, S; MHC Ligands and Peptide Motifs, Chapman & Hall 1998). To elicit an immune reaction, peptides not only have to be able to bind to certain MHC-molecules, they also have to be recognized by T-cells bearing specific TCRs. A further prerequisite for efficient immune reactions is the absence of immunological tolerance against the antigen.

Tumor-associated antigens (TAAs) from which epitopes recognized by CTLs are derived, can be molecules from all protein classes, such as enzymes, receptors, transcription factors, etc., which are upregulated in cells of the respective tumor. Furthermore, antigens can be tumor-specific, i.e. unique to tumor cells, for example as products of mutated genes or from alternative open reading frames (ORFs), or from protein splicing (Vigneron N, Stroobant V, Chapiro J, Ooms A, Degiovanni G, Morel S, van der Bruggen P, Boon T, Van den Eynde B J. Science 2004 Apr. 23; 304 (5670):587-90). Another important class of antigens are tissue-specific antigens, such as "cancer-testis-" (CT)-antigens that are expressed in different kinds of tumors and in healthy tissue of the testis.

Therefore, TAAs are a starting point for the development of a tumor vaccine. The methods for identifying and characterizing the TAAs are based e.g. on the use of CTLs that can be isolated from patients or healthy subjects, or on the generation of differential transcription profiles or differential peptide expression patterns between tumors and normal tissues (Lemmel C., Weik S., Eberle U., Dengjel J., Kratt T., Becker H. D., Rammensee H. G., Stevanovic S. Nat. Biotechnol. 2004 April; 22(4):450-4, T. Weinschenk, C. Gouttefangeas, M. Schirle, F. Obermayr, S. Walter, O. Schoor, R. Kurek, W. Loeser, K. H. Bichler, D. Wernet, S. Stevanovic, and H. G. Rammensee. *Cancer Res.* 62 (20):5818-5827, 2002).

However, the identification of genes overexpressed or selectively expressed in tumor tissues or human tumor cell lines does not provide sufficient information if the corresponding antigen is a useful target for a T-cell based immunotherapy. This is because only an individual subpopulation of epitopes of these antigens are a) presented and b) recognized by T-cells with corresponding TCRs. In addition, immunological tolerance for this particular epitope needs to be absent or negligible. It is therefore important to select only those peptides from overexpressed or selectively expressed proteins that are presented in connection with MHC molecules and are targets of functional T-cells. A functional T-cell is defined as a T-cell that upon stimulation with a specific antigen can be clonally expanded and is able to execute effector functions ("effector T-cell").

T-helper cells play an important role in orchestrating the effector functions of CTLs in anti-tumor immunity. T-helper cell epitopes that trigger a T-helper cell response of the $T_{H1}$ type support effector functions of CD8+ CTLs, which include cytotoxic functions directed against tumor cells displaying tumor-associated peptide/MHC complexes on their cell surfaces. In this way tumor-associated T-helper cell epitopes, alone or in combination with other tumor-associated peptides, can serve as active pharmaceutical ingredients of vaccine compositions which stimulate anti-tumor immune responses.

Since both types of response, CD8- and CD4-dependent, contribute jointly and synergistically to the anti-tumor effect, the identification and characterization of TAAs recognized by CD8+ CTLs (ligand: MHC class I molecule+peptide epitope) and of TAAs recognized by CD4+ T-helper cells (ligand: MHC class II molecule+peptide epitope) are both important in the development of effective tumor vaccines and an effective treatment based on these vaccines.

In Europe, renal cell carcinoma (RCC) ranks as the seventh most common malignancy in men, amongst whom there are 29,600 new cases each year (3.5% of all cancers). Among women, RCC ranks twelfth, with 16,700 cases a year (2.3% of all cancers). RCC is rare before the age of 40, and above this age it is twice as common in men as in women. Incidence by age rises rapidly from less than 2 per 100,000/year in patients under 40 years old to 38 per 100,000/year in the age group 65-69 years. Thereafter, it increases to 46 per 100,000/year in those older than 75 years.

A total of 25-30% of patients with RCC display overt metastases at initial presentation. About one third of patients with RCC will develop metastatic disease over time. Thus, nearly 50-60% of all patients with RCC will eventually present with metastatic disease. Among those with metastatic disease, approximately 75% have lung metastases, 36% lymph node and/or soft tissue involvement, 20% bone involvement, and 18% liver involvement.

RCC is the most lethal carcinoma of the genitourinary tumors with a 65% five-year survival rate compared to the 82% and 100% five-year survival rate for bladder or prostate cancer, respectively (US 1972-2001 data). Average survival rates at 5 years (up to 1999) after diagnosis (1990-1994) for kidney cancer were about 58% in Europe, and RCC was classified by several authors as a cancer with only moderate prognosis. Overall, RCC is fatal in nearly 80% of patients. This figure indicates a strong medical need for effective and early clinical follow-up and treatment for recurrences.

Survival strongly depends on the stage at which the tumor is diagnosed: 5-year survival is only 12% for patients bearing lesions with distant metastases, but 80% for those with localized malignancies.

Globally, colorectal carcinoma (CRC) is the third most common cancer. Colon and rectum cancer account for about 1 million new cases per year, and unlike for most other tumors, numbers are similar in men and women (ratio 1.2:1). In Europe, CRC is the second most common cancer and the second most common cancer-related cause of death in both men and women with approximately 380,000 new cases and about 200,000 disease-related deaths per year. The raw incidence rate in 2002 for men and women was 88.3 and 84.0/100,000, respectively; the raw mortality was 34.8 and 35.2/100,000, respectively. These data clearly reflect the significance of CRC as an enormous source of both individual and societal burden. CRC is a cancer of the elderly population, as the mean age at the time of disease manifestation in men and women is 69 and 75 years, respectively. Besides dietary and lifestyle factors (e.g. obesity, lack of physical exercise, smoking, regular alcohol consumption), other risk factors are familial occurrence of CRC, hereditary types of CRC (familial adenomatous polyposis [FAP], attenuated FAP [attenuated adenomatous polyposis coli; AAPC], hereditary non-polyposis colorectal carcinoma [HNPCC], hamartomatous polyposis syndromes) and inflammatory bowel diseases such as ulcerative colitis or Crohn's disease.

CRC mostly occurs as adenocarcinoma of the mucous membranes in rectum, sigma, colon transversum/descendens, and colon ascendens/caecum. Early colorectal carcinoma may be cured by primary surgery. Distant metastases, however, spread to regional lymph nodes and to liver, lung, and other organs (such as CNS). Due to unspecific symptoms, CRC is often diagnosed at a relatively late stage and approximately 25% of patients with CRC have metastatic disease (mCRC) when first presented to their physicians. An additional 30% of newly diagnosed patients with localized resectable CRC subsequently develop metastatic recurrence.

EP2105740 describes that some proteins, including Apolipoprotein AI (APOA1), are regulated by c-myc overexpression in subjects suffering from or being susceptile to cancer. Consequently, EP2105740 describes the use of the biomarker APOA1 in the diagnosis, prognosis and/or treatment monitoring of cancer, in particular of lung cancer, but not a prediction of the effectiveness of a treatment, let alone an immunotherapy.

WO2010/076322 describes a method for predicting a response to and/or benefit from chemotherapy in a patient suffering from cancer involving (i) classifying a tumor into at least two classes, (ii) determining in a tumor sample the expression of at least one marker gene indicative of a response to chemotherapy for a tumor in each respective class, (iii) and depending on said gene expression, predicting said response and/or benefit; wherein one marker gene is CXCL13. WO2010/076322 also does not describe a prediction of the effectiveness of a treatment, let alone an immunotherapy.

Similarly, WO2010/003773 describes methods for predicting an outcome of cancer in a patient suffering from cancer, said patient having been previously diagnosed as node positive and treated with cytotoxic chemotherapy; wherein one marker gene is CXCL13. WO2010/003773 does not describe a prediction of the effectiveness of an immunotherapy.

EP 1 777 523 A1 relates to the prognosis of the outcome of a cancer in a patient, which prognosis is based on the quantification of one or several biological markers that are indicative of the presence of, or alternatively the level of, the adaptive immune response of said patient against said cancer. Overall, an extremely large number of markers is disclosed. Furthermore, EP 1 777 523 A1 relates to a prognosis (and not prediction) for the outcome of a cancer in a patient, based on the detection and/or the quantification, of one or more biological markers indicative of the presence of, or alternatively of the level of, the adaptive immune response of said patient against said cancer at the tumor site.

Despite the recent progress in the diagnosis and management of many cancers described above, such as, for example, RCC and CRC, still biological markers are needed that can be used to achieve an improved diagnosis, and in particular a prediction of whether a beneficial effect of an immunotherapy can be expected, in order to further improve the survival and to better adjust the treatment of people in need. Furthermore, the markers should also allow for a prediction of the outcome of said treatment of cancer. It is therefore an object of the present invention to provide respective biological markers and diagnostic, predictive and prognostic methods.

SUMMARY OF THE INVENTION

In an aspect of the present invention, said object is solved by providing a method for predicting an effect of an immunotherapy in a cancer patient, comprising a) determining the level of at least one marker selected from the group consisting of Apolipoprotein A1 (ApoA1), CCL17/TARC, eosinophils (in absolute numbers or %), monocytes (in absolute numbers or %), CD95/Fas, aspartate aminotransferase/serum glutamic oxaloaceticacid transaminase (ASAT/SGOT), cancer antigen 19-9 (CA19-9), lactate dehydrogenase (LDH), threonine, immunoglobulin E (IgE), and matrix metalloproteinase 3 (MMP-3) in a sample from said cancer patient, wherein a higher (or increased) level of the marker compared to the median of a given cancer patient population is indicative for a beneficial effect of an immunotherapy for said patient, or b) determining the level of at least one marker selected from the group consisting of CXCL13/BCA-1, neutrophils (in %), interleukin 6 (IL-6) and short-chain acylcarnitines in a sample from said cancer patient, wherein a lower (or decreased) level of the marker compared to the median (+/− 10%) of a given cancer patient population is indicative for a beneficial effect of an immunotherapy for said patient.

BRIEF DESCRIPTION OF THE DRAWINGS

FIG. 1 shows a Kaplan-Meier analysis for the effect of (A) ApoA1, (B) CXCL13/BCA-1, (C) monocytes and (D) CCL17/TARC on overall survival in all patients and subgroups. For each parameter, the upper figure shows the survival of all patients having high (red lines) vs. low (green lines) values of the parameter. The lower figure shows a subgroup analysis (+CY vs −CY) for patients with high values of the parameter (red vs blue lines), and for patients with low values of the parameter (green vs yellow lines).

FIG. 2A shows the distribution of values of the univariate biomarkers ApoA1, CXCL13/BCA-1, monocytes and CCL17/TARC, as indicated in the figure, of the −CY (gray) and +CY (black) group, showing either no T-cell response (no), single peptide response (1) or multipeptide response (>1). Error bars represent the standard error of the mean. FIG. 2B shows a different way of depicting the distribution of values of the multivariate biomarker in patients of the −CY (gray) and +CY (black) group, showing either no T-cell response (no), single peptide response (1) or multipeptide response (>1). Dots represent single values, lines represent the mean.

DETAILED DESCRIPTION OF THE INVENTION

Figure 3A:
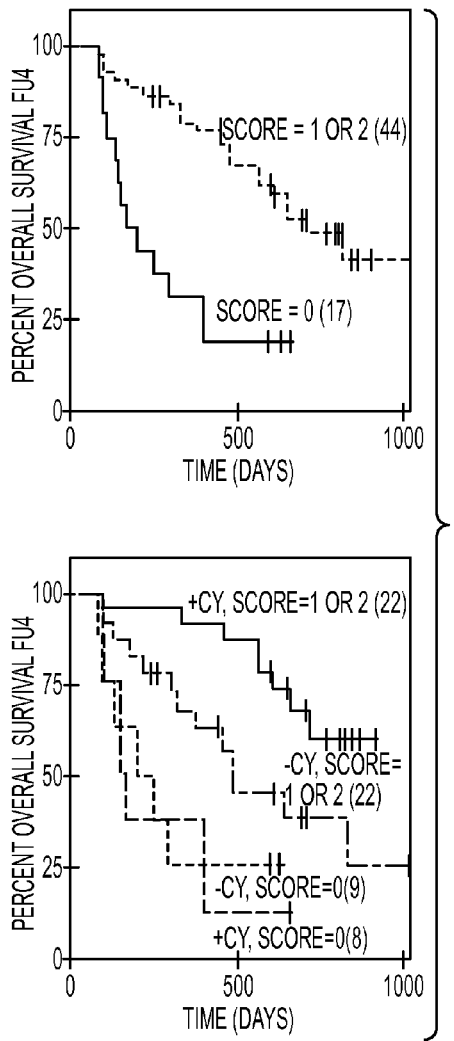
FIG. 3 shows the Kaplan Meier analysis of the effect of a combination of ApoA1 and CCL17/TARC on overall survival in all patients and subgroups. In A), the biomarker-positive population was defined to consist of patients with at least one of the two parameters within the positive range (score=1 or 2), while biomarker-negative patients showed no parameter within the positive range (score=0). In B), the biomarker-positive population was defined to consist only of those patients showing both parameters within the positive range (score=2), while patients with at least one parameter in the negative range (score=0 or 1) were considered biomarker-negative. The upper figures show the survival of all biomarker-positive patients (green lines) vs all biomarker-negative patients (red lines). The lower figures show subgroup analyses (+CY vs −CY) for biomarker-positive patients (green lines vs yellow lines) and biomarker-negative patients (red lines vs blue lines).

In an aspect of the present invention, said object is solved by providing a method for predicting an effect of an immunotherapy in a cancer patient, comprising a) determining the level of at least one marker selected from the group consisting of Apolipoprotein A1 (ApoA1), CCL17/TARC, eosinophils (in absolute numbers or %), monocytes (in absolute numbers or %), CD95/Fas, aspartate aminotransferase/serum glutamic oxaloaceticacid transaminase (ASAT/SGOT), cancer antigen 19-9 (CA19-9), lactate dehydrogenase (LDH), threonine, immunoglobulin E (IgE), and matrix metalloproteinase 3 (MMP-3) in a sample from said cancer patient, wherein a higher (or increased) level of the marker compared to the median of a given cancer patient population is indicative for a beneficial effect of an immunotherapy for said patient, or b) determining the level of at least one marker selected from the group consisting of CXCL13/BCA-1, neutrophils (in %), interleukin 6 (IL-6) and short-chain acylcarnitines in a sample from said cancer patient, wherein a lower (or decreased) level of the marker compared to the median (+/− 10%) of a given cancer patient population is indicative for a beneficial effect of an immunotherapy for said patient. In this embodiment, the invention relates to univariate (also called "single" or "individual") markers for a prediction of an effect, particularly a beneficial effect of an immunotherapy in a cancer patient as described herein, such as longer overall survival, occurrence of single and/or multiple T-cell responses induced by the immunotherapy, retardation of tumor growth, tumor shrinkage or longer progression-free survival.

In the context of the present invention, the terms "marker", "biomarker", "analyte", or "parameter" are used interchangeably, and all relate to the marker(s) as analyzed in the context of the method(s) according to the present invention.

In the context of the present invention, a "prediction" or a "predictive marker" shall be based on markers according to the present invention that are informative for the effectiveness of an immunotherapy of cancer, such as, for example, using the vaccine(s) as described herein.

CXCL13/BCA-1, ApoA1, neutrophils, eosinophils, monocytes, CD95/Fas, ASAT/SGOT, CCL17/TARC, short-chain acylcarnitines and CA19-9 have been identified to be predictive for overall survival, and in some cases for T cell responses, by using univariate analyses.

Preferred is a method according to the present invention, wherein said marker is selected from ApoA1 and/or CCL17/

TARC. CCL17/TARC levels above the median of the respective study population and ApoA1 levels above the median, as indicated by the respective assay provider, (e.g. Rules Based Medicine (RBM), 0.288 mg/ml) are positive.

Preferred is a method according to the present invention, wherein said marker is selected from CXCL13/BCA-1 or monocytes. Nevertheless, also combinations of the markers are included in the scope of the present invention, such as, for example, selected from ApoA1 and CCL17/TARC; ApoA1 and CXCL13/BCA-1; ApoA1, CXCL13/BCA-1, and monocytes; ApoA1, CCL17/TARC, CXCL13/BCA-1, and monocytes; CCL17/TARC and CXCL13/BCA-1; CCL17/TARC, CXCL13/BCA-1, and monocytes; CCL17/TARC, ApoA1 and monocytes; CCL17/TARC, ApoA1 and CXCL13/BCA-1; CCL17/TARC and monocytes; CXCL13/BCA-1 and monocytes; ApoA1 and monocytes. All these marker combinations are particularly preferred.

Further preferred marker combinations are selected from CXCL13/BCA-1, neutrophils %, ApoA1, eosinophils %, eosinophils ABS (absolute), monocytes %, FAS, TARC; LDH, Thr, IL-6, albumin, IgE, MMP-3, CA19-9; monocytes ABS, ASAT, bilirubin, acylcarnitines (scAC); and IL-33. All these marker combinations are also particularly preferred.

ApoA1 is the main protein of high-density lipoprotein (HDL), and can be measured instead of HDL in clinical analyses. Under normal conditions, HDL shows anti-atherosclerotic, anti-oxidant, anti-thrombotic and anti-inflammatory properties. However, under chronic inflammatory/oxidative conditions (as e.g. in chronic infections, autoimmune diseases, metabolic syndrome and cancer), HDL loses these properties and gathers pro-inflammatory properties. In pro-inflammatory HDL (piHDL), ApoA1—a negative acute phase protein—is reduced and other proteins like serum amyloid A (SAA)—a positive acute phase protein—are enriched. Thus, low ApoA1 levels are indicative of chronic inflammatory or oxidative conditions, and they might in turn promote such states, which are known to favor cancer development. Reduced levels of ApoA1 have been reported for many cancers and were also observed in RCC patients of the IMA901-202 (phase II) study cohort. Notably, the related protein ApoA2 has been described as positive prognostic in metastatic RCC, and a mouse model showed a functional involvement of ApoA1 in the suppression of cancer progression (Su et al., 2010; Vermaat et al., 2010). In addition to their cancer-promoting effects, chronic acute phase reactions and oxidative conditions are also known to disfavor adaptive immune responses (Haeryfar and Berczi, 2001; Muller et al., 2008; Vallejo et al., 2004).

CCL17/TARC is a chemokine that has originally been classified as chemokine attracting TH2 cells, but it also has other cellular targets, such as TH1- and TH2-type effector/memory T-cells, particularly those homing to the skin, a subset of CD8+ T-cells, TH17 memory T-cells, NK and NKT cells, dendritic cells, etc. Mouse studies showed that intratumoral CCL17/TARC expression is favorable for immunological rejection. Serum levels might indicate activity of myeloid dendritic cells, macrophages and monocytes, which are major sources of this chemokine. Steady-state production of CCL17 by dendritic cells has been shown to be a prerequisite for their unique function to trigger antigen-independent responses in T-cells. In contrast to conditions like atopic dermatitis and some other allergic or autoimmune conditions, where CCL17/TARC is pathologically enhanced and considered to be indicative for increased TH2 activity, CCL17/TARC levels were within normal ranges in the IMA901-202 study population, and balanced with TH1 cytokines like IL-12 and IFN-gamma.

In the context of the present invention, levels of ApoA1 and levels of CCL17/TARC higher than the median of levels found in advanced RCC patients are considered favorable for treatment success. Patients with at least one factor above the indicated cutoffs (statistically around 75%) are predicted to show improved clinical outcome after vaccination with the cancer vaccine IMA901 (immatics Biotechnologies, Tubingen, Germany), compared to patients showing both factors below the cutoffs. Patients with both factors above the indicated cutoffs (statistically around 25%) are predicted to profit most from treatment. An LLN (lower limit of normal) for ApoA1 depends on the assay used for analysis. Using the Luminex bead-based multiplex technology (RBM), the LLN is 0.288 mg/ml. Using different assays, the LLN has to be adjusted either by using information indicated by the provider, by bridging experiments comparing the assay with the established one, or by measurement with a statistically relevant amount of healthy donor samples. The median of CCL17/TARC and/or ApoA1 levels in a given patient population depends on the population and on the assay used for quantification.

Preferred measurement methods for the markers, and specifically ApoA1 and CCL17/TARC, are selected from immunological assay such as ELISA, bead-, chip- or plate-based multiplex immunoassays, proteomics, or from mass spectrometry, biological assays, electrophoresis, immunonephelometry, immunoturbidimetry, enzymatic assays, colorimetric or fluorometric assays e.g. evaluable by photometry, and fluorescence-associated cell sorting (FACS)-based analyses. Neutrophils, eosinophils and monocytes can be determined by FACS or by other clinically established hematological assays. ApoA1 is highly correlated with HDL cholesterol and can therefore also be determined by all methods used to determine HDL cholesterol.

Furthermore, B-cell attracting chemokine 1 (CXCL13/BCA-1) has been identified as a marker. CXCL13/BCA-1 seems necessary for the organization of lymphocyte assembly in lymphoid organs. Elevated levels are associated with metastasis and poor prognosis in some tumor entities and probably also with impaired anti-tumor immune responses.

Eosinophils, whose levels in percent and absolute numbers were identified as a marker, may, given the contradicting reports on their effects, play several and opposing roles in cancer. Eosinophil recruitment to the tumor is apparently positive in several cases. Eosinophil recruitment to the site of GM-CSF injection was found in case of melanoma.

Monocytes, whose levels in percent and absolute numbers were identified as marker, are recruited to inflammatory sites or sites of GM-CSF administration. They are able to differentiate into macrophages or dendritic cells and can function as APCs themselves. They can replace emigrated tissue dendritic cells such as Langerhans cells. By contrast, high monocytes were described as a negative factor in cancer and IL-2 therapy of RCC, presumably due to reactive oxygen species (ROS) production and inhibition of NK and T cells.

Soluble CD95/Fas is generated by alternative splicing and competes with membrane-bound CD95 for binding of CD95L/FasL. Thus, it may prevent T cell apoptosis, e.g. at the tumor site (tumor counter-attack). It may also counteract the non-apoptotic functions of CD95 signaling, which promote motility and invasiveness of cancer cells. CD95 may also be related to eosinophils, preventing their apoptosis. By contrast, CD95 may also inhibit CD95L-mediated tumor killing by T cells; and in some entities it correlates with high tumor load and worse prognosis.

Neutrophils are a known negative prognostic marker in cancer. Particularly, a high ratio of neutrophils to lymphocytes indicates a negative prognosis in several cancer entities. Here an additional negative predictive influence on the immunotherapy of cancer is suggested. Neutrophils may counteract immune reactions by inhibition of T and NK cells.

Short-chain acylcarnitines are increased in case of a reduced glomerular filtration rate (GFR), indicating greater damage to the kidney which may result in decreased access of blood cells to the tumor (Wanner 1988). On the other hand, acid soluble (free and short-chain) acylcarnitines were reported to be lower in cancer patients than in controls (Sachean 1987).

CA19-9 is an epitope on the sialylated Lewis A structure, a carbohydrate antigen on mucins such as MUC1. The presence in serum might correlate with MUC1 expression in tumor and, thus, with the presence of one of the vaccine antigens. By contrast, serum tumor markers are usually negative prognostic markers.

ASAT/SGOT is an enzyme involved in amino acid metabolism. Like in the case of LDH, increased occurrence in serum serves as indicator of enhanced cell turnover, as it occurs in the case of damage of the liver and other organs, as well as in cancer. Our results confirm that high ASAT/SGOT and LDH are negative prognostic factors in cancer, but unexpectedly also show that they appear to be positively predictive for the outcome of immunotherapies. The reason is yet unclear. It may be speculated that cell death inside the tumor, especially in the form of necrosis, favors immune reactions at the tumor site.

In another aspect thereof, the method according to the present invention further comprises c) determining at least one marker selected from the group consisting of albumin and direct bilirubin in said sample from said cancer patient, wherein a higher level compared to the median (+/−10%) of a given cancer patient population is indicative for a beneficial effect of an immunotherapy for said patient, or d) determining the level of the marker interleukin-33 (IL-33) in said sample from said cancer patient, wherein a lower level compared to the median (+/−10%) of a given cancer patient population is indicative for a beneficial effect of an immunotherapy for said patient.

In this aspect of the present invention, the markers as indicated are used in order to further support the univariate markers as mentioned above in the first aspect of the present invention. The markers thus are used in order to create a "multivariate" marker set or panel for the diagnosis.

Particularly preferred is a method according to the present invention, wherein said multivariate marker set or panel consists of the markers CXCL13/BCA-1, ApoA1, neutrophils, eosinophils (in percent and absolute numbers), monocytes (in percent and absolute numbers), CD95/FAS, ASAT/SGOT, CCL17/TARC, LDH, Thr, IL-6, short-chain acylcarnitines, albumin, bilirubin, IgE, IL-33, MMP-3, and CA19-9.

For the purpose of the present invention the marker reference value is a threshold value for each marker that defines if a patient will benefit from an immune therapy. Depending if the marker is a negative or positive marker, an higher or lower level in the patient compared to the reference value is indicative for a beneficial immune therapy. The reference value is in one embodiment +/−10% of the median concentration observed in a given cancer patient population. More preferred is that the reference value is, depending if it is a negative or positive value, the upper or lower quartile, the upper or lower quintile or the upper or lower dezile of a given cancer patient population. Most preferred is that the reference value of a negative marker, up to which patients are considered to profit from treatment, is the 70th percentile, the 80th percentile, and most preferred the 90th percentile. For positive markers it is most preferred that the reference value, starting from which patients are considered to profit from treatment, is the 30th percentile, the 20th percentile, and most preferred the 10th percentile.

Another important aspect of the present invention relates to a method according to the present invention, wherein said immunotherapy comprises a vaccination with an anti-cancer vaccine, optionally together with an adjuvant, such as, for example, GM-CSF.

Immunotherapy and respective vaccines are described in the state of the art; immunotherapy in cancer patients aims at activating cells of the immune system specifically, especially the so-called cytotoxic T-cells (CTL, also known as "killer cells", also known as CD8+ T-cells), against tumor cells but not against healthy tissue. Tumor cells differ from healthy cells by the expression of tumor-associated and tumor-specific proteins. HLA-molecules on the cell surface present parts of the cellular content to the outside, thus enabling a CTL to differentiate between a healthy and a tumor cell. This is realized by breaking down all proteins inside the cell into short peptides, which are then attached to HLA-molecules and presented on the cell surface. Peptides that are presented on tumor cells, but not or to a far lesser extent on healthy cells of the body, are called tumor-associated peptides (TUMAPs). The antigens from which the epitopes recognized by tumor-specific T-cells are derived can be molecules from all protein classes, such as enzymes, receptors, transcription factors, etc.

However, priming of one kind of CTL is usually insufficient to eliminate all tumor cells. Tumors are very mutagenic and, thus, able to respond rapidly to CTL attacks by changing their protein pattern to evade recognition by CTLs. To counter-attack the tumor evasion mechanisms, a variety of specific peptides is used for vaccination. In this way a broad simultaneous attack can be mounted against the tumor by several CTL clones simultaneously. This may decrease the chances of the tumor to evade the immune response. This hypothesis has been recently confirmed in a clinical study treating late-stage melanoma patients. With only few exceptions, patients that had at least three distinct T-cell responses, showed objective clinical responses or stable disease as well as increased survival, while the vast majority of patients with less than three T-cell responses were diagnosed with progressive disease (Banchereau et al., 2001).

The preferred treatment/composition as used in the context of the methods of the present invention is a peptide-based tumor vaccine. Other preferred treatments include DNA- or RNA-based vaccines, for example as described by Weide et al. (Weide B, Garbe C, Rammensee HG, Pascolo S. Immunol. Lett. 2008 Jan. 15; 115(1):33-42. Epub 2007 Oct. 26) dendritic cell-based vaccines, vaccines using lysates of primary tumor cells or cell lines, or selective components of tumor cells including whole proteins or heat shock proteins. The medicament may be administered directly into the patient, i.e. into the affected organ or systemically i.d., i.m., s.c., i.p., p.o. and i.v., or applied ex vivo to cells derived from the patient or a human cell line which are subsequently administered to the patient, or used in vitro to select a subpopulation of immune cells derived from the patient, which are then re-administered to the patient. The vaccine antigens, e.g. peptides, may be substantially pure, or combined with an immune-stimulating adjuvant (see below) or used in combination with immune-stimulatory cytokines, or be administered with a suitable delivery system, for example liposomes. The peptides may also be conjugated to a suitable carrier such as keyhole limpet haemocyanin (KLH) or mannan (see WO 95/18145 and Longenecker et al (1993)). The peptides may also be tagged, may be fusion proteins, or may be hybrid molecules. The peptides whose sequences are given in the present invention are expected to stimulate CD4+ or CD8+ T cells. However, stimulation of CD+ 8 CTLs is more efficient in the presence of help provided by CD4+ T-helper cells. Thus, for MHC class I epitopes that stimulate CD8+ CTL, the fusion partner or sections of a hybrid molecule suitably provide epitopes which stimulate CD4+ T cells. CD4+-stimulating epitopes are well known in the art and include those identified in tetanus toxoid. In a further preferred embodiment the peptide is a fusion protein, in particular comprising N-terminal amino acids of the HLA-DR antigen-associated invariant chain (Ii). In one embodiment the peptide of the invention is a truncated human protein or a fusion protein of a protein fragment and another polypeptide portion, provided that the human portion includes one or more amino acid sequences of the present invention.

For use, the vaccine may also include one or more adjuvants. Preferred adjuvants are imiquimod, resiquimod, GM-CSF, cyclophosphamide, sunitinib, bevacizumab, interferon-alpha, CpG oligonucleotides and derivates, poly-(I:C) and derivates, RNA, sildenafil, and particulate formulations with PLG or virosomes. As mentioned, the medicament is used for parenteral administration, such as subcutaneous, intradermal, intramuscular or oral administration. For this, the peptides and optionally other molecules are dissolved or suspended in a pharmaceutically acceptable, preferably aqueous carrier. In addition, the composition can contain excipients, such as buffers, binding agents, blasting agents, diluents, flavors, lubricants, etc. The peptides can also be administered together with immune stimulating substances, such as cytokines. An extensive listing of excipients that can be used in such a composition, can be, for example, taken from A. Kibbe, Handbook of Pharmaceutical Excipients, 3rd Ed. 2000, American Pharmaceutical Association and pharmaceutical press. The composition can be used for a prevention, prophylaxis and/or therapy of cancerous diseases, such as, for example, RCC and CRC. Exemplary peptide combinations for vaccines to be used in the context of the present invention are listed in the following tables 1A to 1D, and are herein designated as IMA901, IMA910, IMA941, and IMA950, respectively.

TABLE 1A

IMA901 (e.g. used in RCC)

| SEQ ID No: | Abbrev. | Protein | Sequence |
|---|---|---|---|
| 1 | MMP-001 | Matrix metalloproteinase 7 | SQDDIKGIQKLYGKRS |
| 2 | ADF-002 | Adipophilin | VMAGDIYSV |
| 3 | ADF-001 | Adipophilin | SVASTITGV |
| 4 | APO-001 | Apolipoprotein L1 | ALADGVQKV |
| 5 | CCN-001 | Cyclin D1 | LLGATCMFV |
| 6 | GUC-001 | GUCY1A3 | SVFAGVVGV |
| 7 | K67-001 | KIAA0367 | ALFDGDPHL |
| 8 | MET-001 | c met proto oncogene | YVDPVITSI |
| 9 | MUC-001 | MUC1 | STAPPVHNV |
| 10 | RGS-001 | RGS 5 | LAALPHSCL |

TABLE 1B

IMA910 (e.g. used in colon cancer)

| SEQ ID No: | Abbrev. | Sequence |
|---|---|---|
| 11 | C20-001 | ALSNLEVTL |
| 12 | NOX-001 | ILAPVILYI |
| 13 | ODC-001 | ILDQKINEV |
| 14 | PCN-001 | KLMDLDVEQL |
| 15 | TGFBI-001 | ALFVRLLALA |
| 16 | TOP-001 | KIFDEILVNA |
| 17 | TGFBI-004 | TPPIDAHTRNLLRNH |
| 18 | CEA-006 | SPQYSWRINGIPQQHT |
| 5 | CCN-001 | LLGATCMFV |
| 9 | MUC-001 | STAPPVHNV |
| 1 | MMP-001 | SQDDIKGIQKLYGKRS |
| 19 | CEA-004 | YLSGANLNL |
| 8 | MET-001 | YVDPVITSI |

TABLE 1C

IMA941 (e.g. used in gastric cancer)

| SEQ ID NO | Peptide ID | Sequence |
|---|---|---|
| 20 | CDC2-001 | LYQILQGIVF |
| 21 | ASPM-002 | SYNPLWLRI |
| 22 | UCHL5-001 | NYLPFIMEL |
| 23 | MET-006 | SYIDVLPEF |
| 24 | PROM1-001 | SYIIDPLNL |
| 25 | UQCRB-001 | YYNAAGFNKL |
| 26 | MST1R-001 | NYLLYVSNF |
| 27 | PPAP2C-001 | AYLVYTDRL |
| 28 | SMC4-001 | HYKPTPLYF |
| 29 | MMP11-001 | VWSDVTPLTF |

TABLE 1D

IMA950 (e.g. used in glioblastoma)

| SEQ ID NO | Peptide ID | Sequence |
|---|---|---|
| 30 | CSP-001 | TMLARLASA |
| 31 | FABP7-001 | LTFGDVVAV |
| 32 | NLGN4X-001 | NLDTLMTYV |
| 33 | TNC-001 | AMTQLLAGV |
| 34 | NRCAM-001 | GLWHQTEV |
| 35 | IGF2BP3-001 | KIQEILTQV |

TABLE 1D-continued

IMA950 (e.g. used in glioblastoma)

| SEQ ID NO | Peptide ID | Sequence |
|---|---|---|
| 36 | BCA-002 | ALWAWPSEL |
| 37 | MET-005 | TFSYVDPVITSISPKYG |

TABLE 1E

IMA990a (e.g. used in prostate cancer)

| SEQ ID NO | Peptide ID | Sequence |
|---|---|---|
| 38 | PSA-001 | FLTPKKLQCV |
| 39 | PSA-002 | KLQCVDLHV |
| 40 | PSA-003 | VISNDVCAQV* |
| 41 | PSCA-001 | ALQPGTALL* |
| 42 | PSCA-002 | AILALLPAL |
| 43 | PSMA-001 | LLHETDSAV* |
| 44 | PSMA-002 | ording to c45 |
| 45 | Survivin-004 | ELTLGEFLKL |
| 46 | Survivin-005 | TLPPAWQPFL |
| 47 | TRP-P8-001 | GLMKYIGEV |
| 48 | PROSTEIN-001 | CLAAGITYV |
| 49 | PSMA-001 | NYTLRVDCTPLMYSL |
| 50 | Survivin-001 | TLGEFLKLDRERAKN |

*Optionally left out

Therefore, in yet another preferred aspect of the method according to the present invention, said anti-cancer vaccine is selected from an anti-cancer vaccine comprising at least one immunogenic peptides selected from the group of SEQ ID NO: 1 to 37, for example comprising SEQ ID NO: 1 to 10; SEQ ID NO: 11 to 19 and 1, 5, 8, and 9; SEQ ID NO: 20 to 29, and SEQ ID NO: 30 to 37.

In another aspect of the method according to the present invention, said patient is treated or has been pre-treated. Such pre-treatments may comprise for example curative surgery, radiotherapy and/or chemotherapy. A preferred pre-treatment is a therapy with an anti-cancer agent selected from cytokines, and tyrosine kinase inhibitors (TKI), such as sorafenib and sunitinib, and cyclophosphamide. In this aspect, said cancer treatment can be selected from therapies as described above, preferred is an immunotherapy, preferably comprising the use of an anti-cancer vaccine, optionally together with GM-CSF.

The cancers to be treated can be all cancers which are responsive to immunotherapy, and are preferably selected from RCC, CRC, gastric cancer (GC), melanoma, non-small-cell lung cancer (NSCLC), glioblastoma, and generally adenocarcinoma of any type.

The samples that are analyzed in the context of the present invention can be selected from whole blood, peripheral blood or fractions thereof, serum, buffy coat, tumor tissue, lymphatic fluid, urine, bone marrow, EDTA plasma, heparinized plasma, citrate plasma, heparinized whole blood, and frozen heparinized whole blood. The choice of the sample to be analyzed will also depend on the marker(s) that are to be analyzed, and the person of skill will be able to choose a suitable sample accordingly.

In a preferred embodiment thereof, the method according to the present invention can further comprise a prognosis of an effect of a cancer immunotherapy in a patient, wherein said patient preferably has been pre-treated with cyclophosphamide (as described above). In the context of the present invention, a "prognosis" or a "prognostic marker" shall be based on markers as mentioned herein that are informative for an effect based on a regular or common chemotherapeutic cancer treatment, such as, for example, using taxoles, platinum compounds, and other common agents used in the chemotherapy of cancer(s). The prognosed effect can be selected from overall survival, occurrence of single and/or multiple T-cell responses against the immunotherapy, retardation of tumor growth or progression-free survival. Thus, the markers of the present invention can be used in "mixed" scenarios of predictive and prognostic uses.

In another aspect of the present invention, the method according to the present invention further comprises a monitoring of the effect of said cancer treatment in said patient, comprising repeating the determining step a) and/or b), and optionally c) and/or d), as disclosed herein at least once. Usually, a monitoring is performed in regular intervals during the treatment, such as weekly, twice weekly, or even monthly.

Preferred is a method according to the present invention, wherein said determining comprises at least one method selected from immunoassays, bead-based immunoassays, multiplex immunoassays, ELISA, microarray based assays, epigenetic assays, expression analysis, FACS analysis, mass spectrometry, methods of clinical hematology, and other routine clinical assays like electrophoresis, immunonephelometry, immunoturbidimetry, enzymatic assays, colorimetric or fluorometric assays. All these methods are well known to the person of skill in the art, and described in the literature.

Yet another preferred aspect of the present invention then relates to a diagnostic kit, comprising materials for performing a method according to the present invention as described herein, in one or separate containers, preferably comprising (i) at least one marker-specific antibody specific for ApoA1, CCL17/TARC, Fas, ASAT/SGOT, CA19-9, LDH, IgE, matrix metalloproteinase 3 (MMP-3), CXCL13/BCA-1, neutrophils, interleukin-6 (IL-6), interleukin-33 (IL-33), albumin, and bilirubin, optionally together with (ii) instructions for performing said method.

The kit may further comprise one or more of (iii) a buffer, (iv) a diluent, (v) a filter, (vi) a needle, or (v) a syringe. The container is preferably a bottle, a vial, a syringe or test tube; and it may be a multi-use container. The container may be formed from a variety of materials such as glass or plastic. Preferably the kit and/or container contain/s instructions on or associated with the container that indicates directions for reconstitution and/or use. For example, the label may indicate that the lyophilized formulation is to be reconstituted to certain antibody concentrations as suitable for the above methods, such as ELISA.

Yet another preferred aspect of the present invention then relates to an improved method for treating cancer in a cancer patient in need thereof, comprising a) performing a method according to the present invention as above, and b) administering a suitable anti-cancer immunotherapy to said cancer patient based on the results as obtained in step a), and c) optionally, repeating steps a) and b).

In these therapeutic aspects of the present invention, the methods according to the present invention are used in order to provide improved treatment options in the therapy, in particular immunotherapy, of cancers. The methods according to the invention provide additional and early predictive or predictive and prognostic information regarding the need and the effect of an immunological treatment of cancer, and thus allow for more informed decisions regarding the further treatment of said cancer. Thus, preferred is a method according as above, which further comprises a monitoring of the effect of said cancer treatment in said patient, comprising repeating said determining step at least once.

As described above, preferred treatments or pre-treatments in addition to the immunotherapeutic vaccines as described above are selected from an anti-cancer agent selected from cytokines, sorafenib, sunitinib, cyclophosphamide, and tyrosine kinase inhibitors (TKI). The cancers to be treated can be all cancers which are responsive to immunotherapy, and are preferably selected from renal cell carcinoma (RCC), colorectal cancer (CRC), gastric cancer (GC), melanoma, non-small-cell lung cancer (NSCLC), glioblastoma, and adenocarcinoma.

It should be understood that the features of the invention as disclosed and described herein can be used not only in the respective combination as indicated but also in a singular fashion without departing from the intended scope of the present invention.

The invention will now be described in more detail in the examples with reference to the sequence listing. The following examples are provided for illustrative purposes only and are not intended to limit the invention.

SEQ ID NO: 1 to 50 show the amino acid sequences of the peptides as listed above in table 1A to 1E.

TABLE 2

| Univariate biomarkers | HR and logrank p-values | | | |
|---|---|---|---|---|
| | ApoA1 | CXCL13/ BCA-1 | Monocytes | CCL17/ TARC |
| All patients, Biomarker-positive vs -negative | 0.42 (0.01) | 0.39 (0.006) | 0.44 (0.012) | 0.41 (0.011) |
| +CY group, Biomarker-positive vs -negative | 0.3 (0.017) | 0.25 (0.004) | 0.24 (0.001) | 0.18 (0.003) |
| −CY group, Biomarker-positive vs -negative | 0.6 (0.253) | 0.7 (0.448) | 0.93 (0.874) | 0.67 (0.392) |
| Biomarker-positive group, +CY vs −CY arm | 0.36 (0.061) | 0.35 (0.051) | 0.29 (0.014) | 0.22 (0.017) |
| Biomarker-negative group, +CY vs −CY arm | 0.84 (0.696) | 1.07 (0.876) | 1.31 (0.538) | 0.85 (0.715) |
| Interaction | 0.43 (0.24) | 0.3271 (0.13) | 0.22 (0.03) | 0.26 (0.094) |
| Parameter is favourable if values are high/low | high | low | high | high |
| Cutoff | 0.264 mg/ml (MEDIAN) | 64.21 pg/ml (MEDIAN) | 7.7% (MEDIAN) | 161.99 pg/ml (MEDIAN) |

Table 2 shows hazard ratios (HR) and logrank p-values (Cox proportional hazard analysis) for prediction of overall survival by the univariate biomarkers in all patients and +/−CY subgroups, HR and logrank p-values for the effect of cyclophosphamide pre-treatment within biomarker-positive and biomarker-negative patients, and for the interaction effect of the biomarkers with cyclophosphamide pre-treatment.

TABLE 3

| | p-values (Welch's t-test) | | | |
|---|---|---|---|---|
| | ApoA1 | CXCL13/ BCA-1 | Monocytes | CCL17/ TARC |
| All patients, responders | 0.016 | 0.28 | 0.24 | 0.032 |
| All patients, multipeptide responders | 0.000074 | 0.031 | 0.34 | 0.0028 |
| +CY group, responders | 0.014 | 0.064 | 0.0021 | 0.013 |
| +CY group, multipeptide responders | 0.42 | 0.29 | 0.37 | 0.53 |
| −CY group, responders | 0.034 | 0.15 | 0.065 | 0.017 |
| −CY group, multipeptide responders | 0.00014 | 0.13 | 0.73 | 0.068 |
| Parameter is favorable if values are high/low | high | low | high | high |

Table 3 shows p-values calculated by univariate statistical analysis (Welch's t test) for the prediction of T cell responses and multipeptide T cell responses by the selected parameters for all patients and +/−CY subgroups.

TABLE 4

| Multivariate biomarker (OSCY_CHEAP_UNIF_20) | HR (95% CI) and logrank p-values |
|---|---|
| All patients, Biomarker-positive vs -negative | 0.47; P = 0.041 |
| +CY group, Biomarker-positive vs -negative | 0.07; P = 0.000008 |
| −CY group, Biomarker-positive vs -negative | 1.58; P = 0.203 |
| Biomarker-positive group, +CY vs −CY arm | 0.08 (0.02-0.38); P = 0.000135 |
| Biomarker-negative group, +CY vs −CY arm | 2.5 (0.95-6.58); P = 0.055 |
| Interaction | 0.032 (0.0055-0.1863); P = 0.000128 |
| Parameter is favourable if values are high/low | High |
| Cutoff | 0.019076043 points |

Table 4 shows hazard ratios (HR) and logrank p-values for prediction of overall survival by the multivariate biomarker in all patients and +/−CY subgroups, HR and logrank p-values for the effect of cyclophosphamide pre-treatment within biomarker-positive and biomarker-negative patients, and for the interaction effect of the biomarker with cyclophosphamide pre-treatment.

EXAMPLES

1. Introduction

IMA901 is a peptide-based vaccine designed to induce specific T cell reactions against peptide-MHC complexes found on RCC. The IMA901-202 (phase II) study used univariate and multivariate analyses to identify parameters which alone or in combination serve as predictive biomarkers for the success in terms of immune response induction and prolongation of overall survival of IMA901 treatment of metastatic RCC patients.

To achieve this, around 450 parameters (patient- or tumor-related parameters as well as analytes measured in serum or urine and cellular parameters) were analyzed using pre-treatment samples of the IMA901-202 (phase II) study population. For multivariate analyses, which selected a set of several parameters, those parameters that required preparation of peripheral blood mononuclear cells (PBMCs) were not included in order to limit measurement costs in future trials. Parameters were analyzed for their association with overall survival and T-cell responses.

Since IMA901 treatment showed much greater effects on overall survival after cyclophosphamide pre-treatment, and since only in the +CY arm the presence of immune responses was associated with improved overall survival, the +CY arm was considered the active arm of the study and compared to the −Cy arm as control. Thus, parameters were chosen that showed interaction with cyclophosphamide pre-treatment and/or that predicted overall survival better in the +CY arm than in the −CY arm. Thereby, the selection of purely prognostic markers, which by definition would show association with overall survival in both arms, was avoided.

2. Comparison of Study Patients with Age-Matched Healthy Donors

For comparison of pre-treatment levels with healthy donors, only intention-to-treat (ITT) patients below the age of 70 were selected to match the oldest healthy control donors. The resulting groups of patients (N=52) and healthy donors (N=22) were balanced with respect to age, gender and CMV (cytomegalovirus) seropositivity.

3. Materials and Methods

Sample Collection

All samples were collected before any therapeutic study intervention, either three days before vaccination and immediately before administration of cyclophosphamide in the +CY arm, or immediately before vaccination. Serum samples were taken using a serum/gel-VACUTAINER (Becton Dickinson, 5 ml), inverted and incubated for a minimum of 30 minutes. Tubes were centrifuged for 15 minutes at least 1200×g, and serum (approximately 2 ml) was transferred into a NUNC cryotube (3.6 ml). Cryotubes were stored immediately at <−20° C. until measurement. EDTA blood for analysis of haematology parameters was collected in 3 ml EDTA-VACUTAINERs, which were not centrifuged, and stored at ambient temperature until analysis. Urine was collected shortly before vaccination. For dipstick examination, only fresh urine was used. Citrated plasma for analysis of coagulation was collected approximately two weeks before vaccination. Samples were taken using a citrate-VACUTAINER and centrifuged within 30 minutes at least 1200×g at ambient temperature. Supernatant plasma was transferred into microtubes.

Measurements

Biomarker measurement methods included ELISA, multiplex immunoassays, epigenetic assays, mass spectrometry, FACS analyses, routine clinical methods of haematology, clinical chemistry and urine analysis, and other methods. The parameters that were finally selected were measured by multiplex assays provided by RBM (ApoA1, CD95/FAS, IL-6, IgE, MMP-3, CA19-9), Millipore (CXCL13/BCA-1, CCL17/TARC), IL-33), and by mass spectrometry provided by Biocrates (threonine, short-chain acylcarnitines). Further parameters were provided by the central laboratory and were measured by routine methods of haematology (neutrophils, eosinophils, monocytes) and clinical chemistry (ASAT/SGOT, LDH, albumin, bilirubin).

Assessment of T-Cell Responses.

As besides overall survival the occurrence of one or multiple T-cell responses had to be tested for association with biomarkers, specific T-cell responses were measured before and after several times after vaccination, using ELISPOT assays and tetramer stainings with the respective peptide-MHC complexes.

Univariate Statistical Analysis:

The association of parameters with T-cell responses was assessed using Welch's t test. Parameters predictive for T cell responses in all patients and/or within the +CY group with $p<0.05$ were considered significant.

The interaction of parameters with CY-pre-treatment was assessed using the Cox proportional hazards model. Candidates showing an interaction p value of <0.05 at any cutoff value that was not at the extreme ends of the distribution (i.e. selecting or de-selecting >~5% of patients) were considered as interesting.

Moreover, to exclude parameters with significant interaction due to inverse association of cyclophosphamide pre-treatment with overall survival in the unfavorable biomarker group, an additional criterion was significant association ($p<0.05$) with overall survival in the positive biomarker group. A significant ($p<0.05$) association with overall survival in the +CY group, but not in the −CY group was considered to be an additional hint for the predictive instead of prognostic quality of a parameter.

Further criteria for parameter selection were based on their biology and on the persistence of their pattern of interaction with cyclophosphamide pre-treatment and association with overall survival in the +CY but not in the −CY arm in subgroups of patients, such as TKI-pre-treated and cytokine-pre-treated patients.

Correlations between the parameters were calculated. Parameters that were highly correlated with others in the remaining set (adjusted p-value<0.005) were excluded.

After identifying single parameters using these steps, it was tested whether and which combinations of these parameters showed best performance with respect to prediction of overall survival and T-cell responses, and for stability in the subgroups of patients indicated above.

Multivariate Statistical Analyses:

Multivariate biomarkers were determined according to a Cox proportional hazard model, whose properties and extensions are described in the following.

As covariates in the generalized linear model, all parameters were considered, though linearly transformed to zero mean and unit variance ("standardized" parameters) in order to avoid undue influence for parameters that are represented in small units. Only parameters that did not require PBMC isolation were included, to limit measurement costs for the set. As the corresponding maximum partial likelihood problem was under-determined, i.e. the number of parameters exceeded the number of patients; the model was augmented with a Gaussian prior, which limits the relative influence of each parameter in the optimal biomarker. The corresponding maximum a-posteriori (MAP) optimization is also known to improve the predictive performance of the results ("regularization") over the maximum likelihood approach. The model was further augmented by a Laplacian prior, which causes the optimization to use only a subset of the considered parameters. By this means, the number of parameters included in the biomarker was limited to 20.

Further it was desired that the multivariate biomarker be not predictive in the −CY arm, or at least be less predictive for those patients than for the +CY arm. In order to achieve this, repeatedly predictive models were optimized on the −CY arm, and the resultant directions projected out from the parameter space, until only essentially unpredictive directions remained. The biomarker itself was then determined on the remaining subspace of the parameters on the +CY arm. In order to assess the predictive accuracy of the biomarker, the entire optimization process was applied in a leave-one-out fashion. The predictions for all patients were computed in the way, collected, and then compared to the known survival times.

Results: Univariate Analysis

Selection of Parameters

Of the around 450 parameters tested, 59 significantly predicted the occurrence of T-cell responses either on all patients and/or in the +CY group of patients. 118 parameters showed significant interaction with cyclophosphamide pre-treatment at their optimal cutoff values. Using the above-mentioned criteria of T-cell response prediction, interaction with cyclophosphamide pre-treatment, better association with overall survival in the +CY than in the −CY group, non-redundancy with other parameters, and presence of a reasonable biological rationale, four parameters (ApoA1, CXCL13/BCA-1, monocytes and CCL17/TARC) could be identified as preferred univariate biomarker candidates.

Definition of Cutoffs

For each of the four parameters identified as described above, a discrete cutoff was defined, separating patients into two groups (positive or negative for the biomarker) which showed a significantly different outcome of IMA901 treatment. The selection of cutoff values was required, as the parameters, although associated with overall survival and T-cell responses in a continuous rather than discrete fashion, should be used for yes/no treatment decisions. For that reason, appropriate cutoffs should a) include sufficient patients and should b) be objective.

In case of ApoA1, for which more than 50% of IMA901-202 patients showed pathologically reduced levels, the cutoff was chosen to be the LLN determined in healthy donors as indicated by the assay provider (RBM, 0.288 mg/ml), identifying the patients with ApoA1 levels within the normal range as biomarker-positive group. This cutoff value was close to the median of the IMA901-202 study patients (0.264 mg/ml). Thus, this cutoff is maximally objective and associated with the biological rationale for ApoA1. Alternatively, for ApoA1 also the median was used. The other parameters were largely within normal ranges in IMA901-202 patients. For these parameters, the median of the study population was chosen as cutoff, as this is also objective and includes sufficient (50%) patients.

Prediction of Overall Survival and T-Cell Responses by Single Univariate Biomarkers Cox proportional hazard analyses showed that all of the four parameters selected by univariate analyses significantly predict overall survival in all patients and in the subgroup of patients pre-treated with cyclophosphamide, but not in the subgroup that did not receive cyclophosphamide pre-treatment (Table 2, FIG. 1). In the biomarker-positive groups, as defined by the respective cutoff of the biomarker value, cyclophosphamide pre-treatment showed a significantly ($p<0.05$) positive effect on overall survival (CCL17/TARC, monocytes) or a trend ($p<0.1$) towards a positive effect on overall survival (ApoA1, CXCL13/BCA-1). Interaction analysis showed that the effect of cyclophosphamide-pretreatment was significantly different ($p<0.05$) in patients classified as positive or negative for their monocyte levels. CCL17/TARC showed a trend for interaction with cyclophosphamide pre-treatment. ApoA1 and CXCL13/BCA-1 did not reach significance at the chosen cutoffs.

Notably, in the +CY group, the best hazard ratio (HR) could be achieved if patients were classified by their CCL17/TARC levels (Table 2, HR=0.18, p=0.003). Vice versa, CCL17/TARC-positive patients profited most from cyclophosphamide pre-treatment (Table 2, HR=0.22, p=0.017).

CCL17/TARC was also exceptional in consideration of the fact that 75% of CCL17/TARC-positive cyclophosphamide-pre-treated patients were still alive at the end of the study (FIG. 1D).

The pattern observed with respect to overall survival prediction remained stable for the subpopulations of patients that had been pre-treated with TKI or cytokines (data not shown).

With respect to T cell response prediction, CCL17/TARC and ApoA1 performed best, both significantly predicting responders in all patients and both +CY and −CY subgroups, and predicting multipeptide responders in all patients. By contrast, CXCL13/BCA-1 and monocytes were weak response predictors (Table 3).

5. Results: Multivariate Analysis

Selection of Parameters

A 20-parameter biomarker set predicting overall survival in the +CY group of patients better than in the −CY group upon treatment with IMA901 was calculated for the total patient population. Parameters included in this set are listed in Table 4. They include cytokines, chemokines and other proteins measurable in serum, cellular parameters measurable by standard hematology assays, and metabolomic parameters measurable by mass spectrometry. Besides the optimization for all patients (train version), the biomarker set was calculated using leave-one-out cross-validation (test version). The latter analysis is more relevant, as it grants robustness of the results in follow-up studies. Data shown in these experiments represent the test results.

TABLE 5

| Weight | Rank | Parameter name |
|---|---|---|
| −47.3867 | 1 | CXCL13/BCA-1 |
| 38.38821 | 2 | ApoA1 |
| −38.1861 | 3 | Neutrophils (%) |
| 34.36199 | 4 | Eosinophils (%) |
| 34.10915 | 5 | Monocytes (%) |
| 33.89069 | 6 | CD95/FAS |
| 32.72272 | 7 | ASAT/SGOT |
| 32.01683 | 8 | CCL17/TARC |
| 31.7325 | 9 | LDH |
| 31.47377 | 10 | Thr |
| −31.3839 | 11 | IL-6 |
| −31.2785 | 12 | Short-chain acylcarnitines |
| 30.83843 | 13 | Albumin |
| 30.78772 | 14 | Eosinophils (abs.) |
| 29.57142 | 15 | Monocytes (abs.) |
| 28.89882 | 16 | Bilirubin (direct) |
| 28.63935 | 17 | IgE |
| −27.8701 | 18 | IL-33 |
| 27.72058 | 19 | MMP-3 |
| 27.204 | 20 | CA19-9 |

Table 5 shows the parameters included in the 20-parameter multivariate biomarker, and the weights and ranks indicating their relative importance in the set.

The biomarker value for each patient is a linear combination of the values measured for the 20 parameters included. The constant factors in this equation were chosen in a way that the median of the biomarker distribution was close to zero. The biomarker values calculated in this way were approximately normally distributed in the population of IMA901-202 patients, and they were equally distributed between patients of the +CY and −CY arm.

Figure 5A:
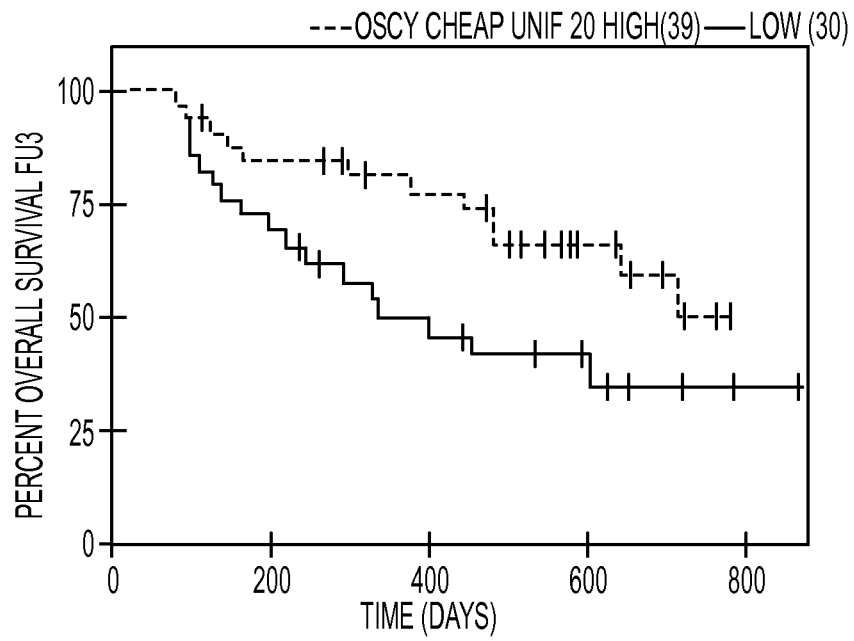
FIG. 5 shows a Kaplan-Meier analysis for the effect of the multivariate biomarker on overall survival. The upper figure shows the survival of all patients having high (red lines) vs. low (green lines) values of the parameter. The lower figure shows a subgroup analysis (+CY vs −CY) for patients with high values of the parameter (red vs blue lines), and for patients with low values of the parameter (green vs yellow lines). The value of 0.019076043 points was used as cut-off separating biomarker high and low patients.
Figure 5B:
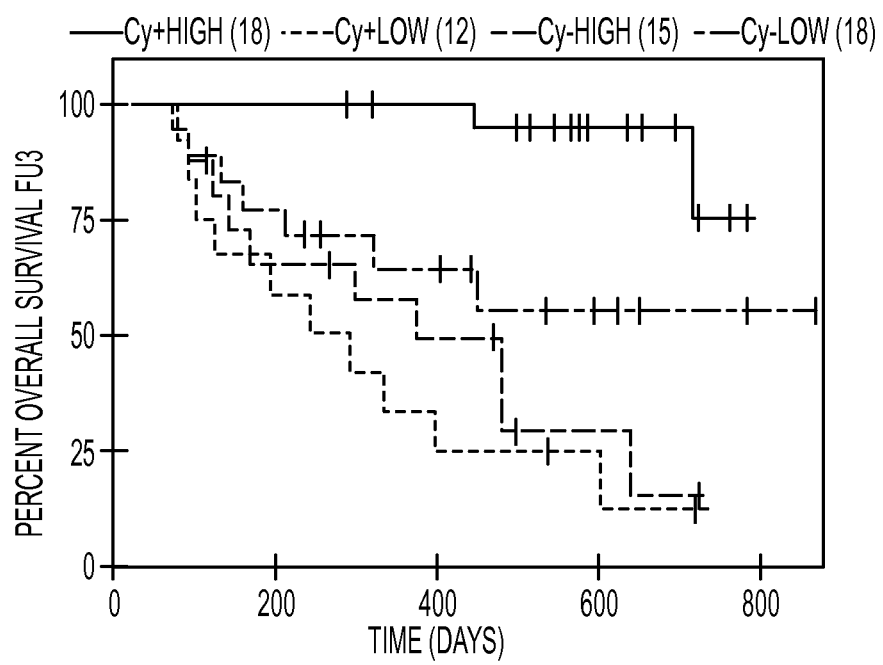

Prediction of Overall Survival and T-Cell Responses by the Multivariate Parameter Set To demonstrate the predictive power of the biomarker, a survival analysis was performed by subdividing patients in two groups according to their biomarker value. The median of the density distribution of the biomarker over the whole patient population was chosen as cutoff, including 50% of patients with values above this cutoff in the biomarker-positive group. In the +CY group of patients, biomarker-positive patients profited highly significantly from vaccination, while the biomarker showed no effect in the −CY arm. Vice versa, in the biomarker-positive group, cyclophosphamide pre-treatment resulted in significantly higher overall survival, while the effect was not significant or even (tendentially) inverse in the biomarker-negative group (Table 4; FIG. 5). Correspondingly, there was a highly significant interaction between the multivariate biomarker and cyclophosphamide pre-treatment.

Figure 6A:
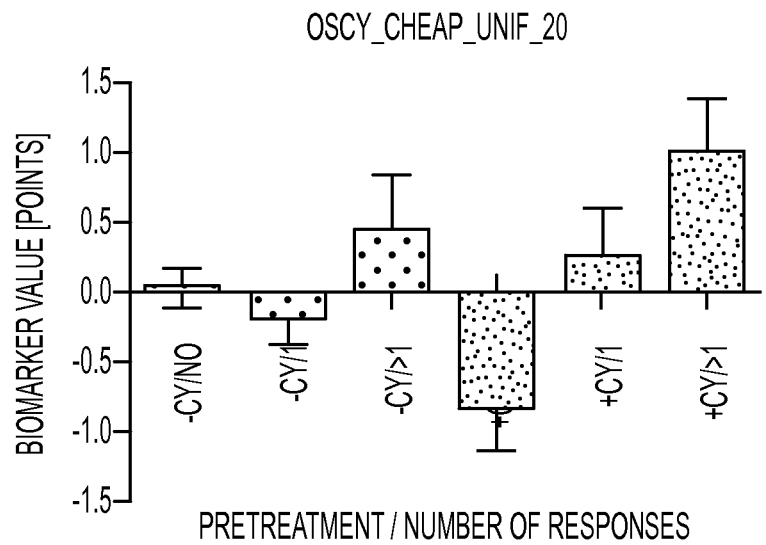
FIG. 6A shows the mean values of the multivariate biomarker in patients of the −CY (gray) and +CY (black) group, showing either no T-cell response (no), single peptide response (1) or multipeptide response (>1). Error bars represent the standard error of the mean.
Figure 6B:
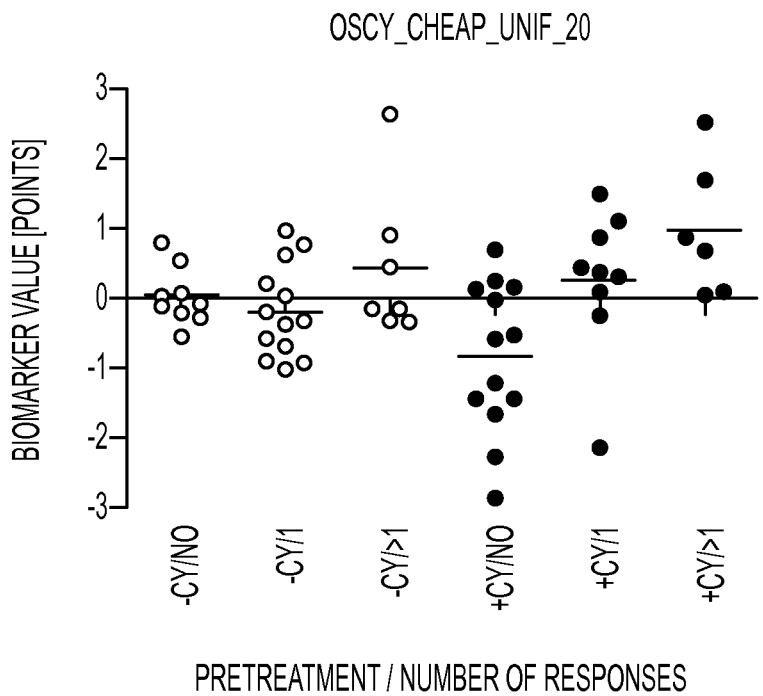
FIG. 6B shows a different way of depicting the distribution of values of the multivariate biomarker in patients of the −CY (gray) and +CY (black) group, showing either no T-cell response (no), single peptide response (1) or multipeptide response (>1). Dots represent single values, lines represent the mean.

Although the biomarker had not been optimized to predict immune responses, the inventors tested whether the distribution of biomarker values was associated with the presence or absence of T-cell responses as well. There was in fact a tendency towards higher biomarker values in responder- and multipeptide-responder groups, particularly in the +CY group of patients (FIG. 6).

Prediction of Overall Survival and T-Cell Responses by a Combination of Parameters Single parameters can be combined in a way that patients can be assigned a biomarker score, depending on the values of all the parameters included in the combination. In case of a two-parameter combination, each parameter could be either positive or negative according to its cutoff, and patients could have a biomarker score of two (both parameters positive), one (one parameter positive) or zero (no parameter positive) with respect to the combined marker.

Combining several parameters to calculate a biomarker score may be favorable for several reasons. First, it leads to greater robustness, as a) the problem of fixed cutoffs in spite of a continuous association of parameters with outcome is overcome to some extent, b) the impact of measurement outliers is reduced, and c) a greater number of parameters enables insight into a larger number of biological processes that may be relevant for anti-cancer immunity. Second, a score model enables more flexibility with respect to patient selection: While a single parameter with the median as objective cutoff would necessarily select only 50% of patients for treatment, a two-parameter score (with cutoff of the single parameters at the median of the distribution) divides patients in three groups. If only patients without positive markers (i.e. with a biomarker score of zero) are excluded, about 75% of patients would be included in the treatment group. However, if no significance is reached in this group, the patients with scores of zero and one can be excluded, leaving the about 25% patients showing a biomarker score of two in the treatment group.

Figure 3B:
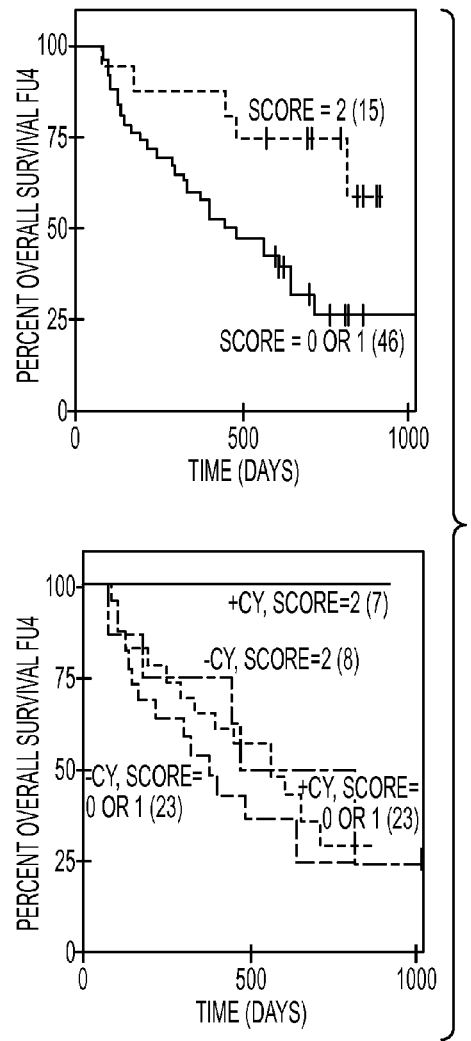
Figure 4A:
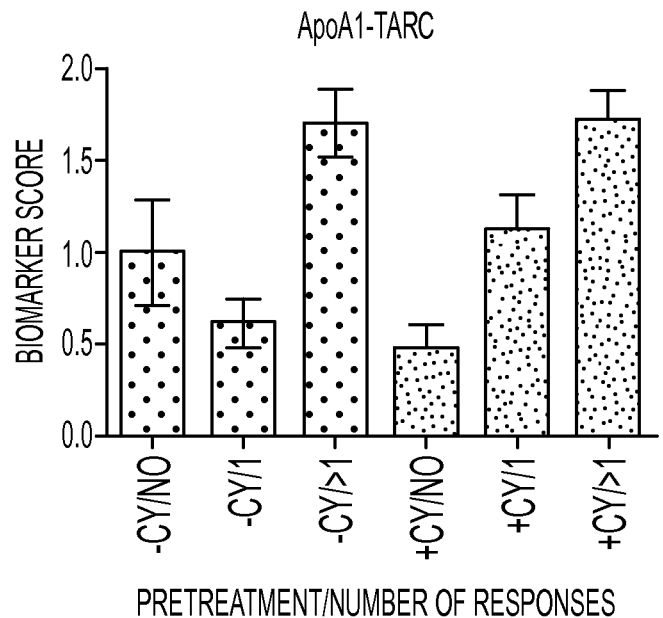
FIG. 4A shows the mean of the marker consisting of the combination of ApoA1 and CCL17/TARC in patients of the −CY (gray) and +CY (black) group, showing either no T-cell response (no), single peptide response (1) or multipeptide response (>1). Error bars represent the standard error of the mean.
Figure 4B:
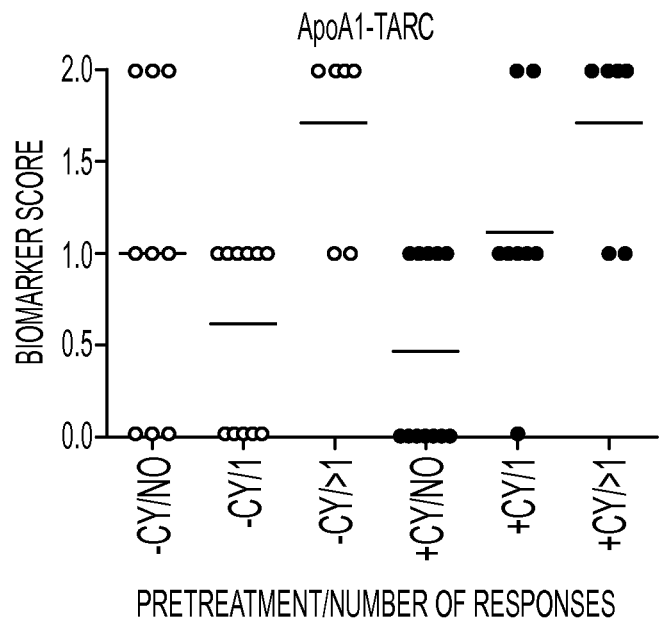
FIG. 4B shows a different way of depicting the distribution of values of the binary biomarker in patients of the −CY (gray) and +CY (black) group, showing either no T-cell response (no), single peptide response (1) or multipeptide response (>1). Dots represent single values, lines represent the mean.

For these reasons, it was tested whether a combination of the single parameters identified above leads to better performance with respect to prediction of overall survival and T-cell responses. Moreover, the stability of the effect in the patient subpopulations indicated above was assessed. Several combinations of markers outperformed the use of single parameters in these respects, the best of which was a combination of ApoA1 and CCL17/TARC (FIG. 3, FIG. 4).

6. Marker Levels:
6.1 Serum Levels of ApoA1

| Condition | Source | ApoA1 [mg/ml]; Range or Average +/− STD |
|---|---|---|
| Healthy controls | (Riesen, 2008) | 1.0-1.5 |
| | Manufacturer (RBM) | 0.288-1.17 |
| IMA901-202 study | Range (median) | 0.0808-0.514 (0.264) |
| | Average +/− STD | 0.27 +/− 0.09 |

6.2 Serum Levels of CCL17/TARC

| Condition | Source | TARC [pg/ml]; Range or Average +/− STD |
|---|---|---|
| Healthy controls | (Shimada et al., 2004) | 200 +/− 100 |
| | (Fujii et al., 2004) | 101 +/− 81 |
| | (Sugawara et al., 2002) | 31.9 +/− 14.8 |
| | (Sekiya et al., 2002) | 88.8 +/− 58.2 |
| | (Echigo et al., 2006) | 93.3 +/− 25.3 |
| | (Saeki and Tamaki, 2006) | 215.34 +/− 26.79 |
| Atopic dermatitis | (Leung et al., 2003) | 1125-3070 (1469) |
| | (Shimada et al., 2004) | 96400 +/− 38100 |
| | (Sugawara et al., 2002) | 325 +/− 287 |
| | (Saeki and Tamaki, 2006) | 2338.7 +/− 301.83 |
| Asthma | (Sugawara et al., 2002) | 271 +/− 264 |
| | (Sekiya et al., 2002) | 192.0 +/− 143.6 |
| Allergic rhinitis | (Sugawara et al., 2002) | 147 +/− 101 |
| Systemic sclerosis | (Fujii et al., 2004) | 313 +/− 294 |
| Dermatomyositis | | 262 +/− 291 |
| SLE | | 254 +/− 326 |
| IMA901-202 study | Range (median) | 25.5-623 (162) |
| | Average +/− STD | 174 +/− 118 |

6.3 Serum Levels of BCA-1

| Condition | Source | BCA-1 [pg/ml]; Range or Average +/− STD |
|---|---|---|
| Healthy controls | (Panse et al., 2008) | ~40 |
| | (Sansonno et al., 2008) | 48.2 +/− 11.0 |
| Disease | (Panse et al., 2008), breast cancer | ~80 |
| | (Sansonno et al., 2008), HCV-infected patients with and without mixed cryoglobulinemia | 273.6 +/− 98; 113.9 +/− 40.2 |
| IMA901-202 study | Range (median) | 13.09-1429.6 (64.21) |
| | Average +/− STD | 114.23 +/− 196.98 |

6.4 Levels of Neutrophils in Percent and Absolute Numbers

| Condition | Source | Neutrophils; Range or Average +/− STD |
|---|---|---|
| Healthy controls | LKF Kiel Laboratory, Germany | 34-71%; 1.5-6.2 × 10^9/L |
| Disease | (Rashid et al., 2010), oesophageal cancer | 58-71% |
| | (Donskov et al., 2006), RCC | 2.6-15.9 × 10^9/L |
| IMA901-202 study | Range (median) | 47-86.9 (67.3)%; 2.18-10.39 (4.44) × 10^9/L |
| | Average +/− STD | 68.05 +/− 8.2%; 4.88 +/− 1.86 × 10^9/L |

6.5 Levels of Eosinophils in Percent and Absolute Numbers

| Condition | Source | Eosinophils; Range or Average +/− STD |
|---|---|---|
| Healthy controls | LKF Kiel Laboratory, Germany | 0-7%; 0.04-0.6 × 10^9/L |
| | (Simon and Simon, 2007) | 0-0.4 × 10^9/L |
| Disease | (Moroni et al., 2000), RCC | 0.15 +/− 0.1 × 10^9/L |
| IMA901-202 study | Range (median) | 0.2-6.5 (2)%; 0.02-0.55 (0.12) × 10^9/L |
| | Average +/− STD | 2.35 +/− 1.62% 0.16 +/− 0.13 × 10^9/L |

6.6 Levels of Monocytes in Percent and Absolute Numbers

| Condition | Source | Monocytes; Range or Average +/- STD |
|---|---|---|
| Healthy controls | LKF Kiel Laboratory, Germany | 4-13%; 0.2-0.9 × 10^9/L |
| Disease | (Sasaki et al., 2006), hepatocellular carcinoma | 0.03-1.04 × 10^9/L |
| | (Donskov et al., 2006), RCC | 0.69-0.74 × 10^9/L |
| IMA901-202 study | Range (median) Average +/- STD | 3.1-17.7 (7.6)%; 0.2-1.31 (0.48) × 10^9/L 8.19 +/- 3.15%; 0.57 +/- 0.25 × 10^9/L |

6.7 Serum Levels of Soluble CD95/FAS

| Condition | Source | CD95/FAS [ng/ml]; Range or Average +/- STD |
|---|---|---|
| IMA901-202 study | Range (median) Average +/- STD | 4.09-20.4 (9.89) 9.76 +/- 3.06 |

6.8 Serum Levels of ASAT/SGOT

| Condition | Source | ASAT/SGOT [U/L]; Range or Average +/- STD |
|---|---|---|
| Healthy controls | LKF Kiel | 12-35.4 |
| IMA901-202 study | Range (median) Average +/- STD | 14-109 (23.5) 27.9 +/- 17.3 |

6.9 Serum Levels of LDH

| Condition | Source | LDH [U/L]; Range or Average +/- STD |
|---|---|---|
| Healthy controls | LKF Kiel | 129-230 |
| IMA901-202 study | Range (median) Average +/- STD | 94-734 (161.5) 190.63 +/- 98.97 |

6.10 Serum Levels of Threonine

Thr Min/Max: 21-157 µM
Thr AVG/STD: 84.5+/−24.1 µM
MEDIAN: 82 µM

6.11 Serum Levels of Albumin

Normal serum ranges and deviations under pathological conditions:
Laboratory: Albumin 35-50 g/l (3.5-5 g/dl)

| parameter | AVG (l.val_float) | unit | STD (l.val_float) | MIN (l.val_float) | MAX (l.val_float) | MEDIAN (l.val_float) |
|---|---|---|---|---|---|---|
| albumin_blood | 39.95 | G/L | 4.39 | 26 | 48 | 41 |

6.12 Levels of Direct Bilirubin

Laboratory: 0-5.1 µM
Serum range in IMA-901 study:
Min/Max: 0.5-4.4 µM (21 distinct values)
AVG/STD: 2.0-0.89 µM
MEDIAN: 1.7 µM

6.13 Levels of MMP-3

Range in IMA-901 study:
Min/Max: 1.85-41.2 ng/ml (only 3 were above 17; 58 discrete values)
AVG/STD: 8.5+/−6.0 ng/ml
MEDIAN: 6.7 ng/ml
Normal serum ranges: Range according to manufacturer: 0.2-2.17 ng/ml

6.14 Levels of CA19-9

| High Serum Range (provider) | parameter | AVG | unit | STD | MIN | MAX | MED | Count |
|---|---|---|---|---|---|---|---|---|
| 52 | Cancer_Antigen_19-9 | 15.63 | U/ml | 29.73 | 0 | 167 | 5.94 | 45 |

6.15 Levels of IgE

| parameter | AVG (l.val_float) | unit | STD (l.val_float) | MIN (l.val_float) | MAX (l.val_float) | MEDIAN (l.val_float) |
|---|---|---|---|---|---|---|
| IgE | 104.09 | ng/ml | 261.00 | 0 | 1362 | 22.5 |

Provider (RBM): normal up to 606 ng/ml IgE

6.16 Levels of IL-6

| parameter | AVG (l.val_float) | unit | STD (l.val_float) | MIN (l.val_float) | MAX (l.val_float) | MEDIAN (l.val_float) |
|---|---|---|---|---|---|---|
| IL-6 | 16.32 | pg/ml | 67.65 | 0 | 532 | 2.86 |

Provider (RBM): normal up to 42.6 pg/ml IL-6
6.17 Levels of IL-33

| parameter | AVG (l.val_float) | unit | STD (l.val_float) | MIN (l.val_float) | MAX (l.val_float) | MEDIAN (l.val_float) |
|---|---|---|---|---|---|---|
| IL-33 | 166.95 | pg/ml | 293.28 | 55.0672 | 1867 | 75.73 | n.a. normal ranges

REFERENCE LIST

Donskov F, Hokland M, Marcussen N, Torp Madsen H H, von der M H (2006). Monocytes and neutrophils as 'bad guys' for the outcome of interleukin-2 with and without histamine in metastatic renal cell carcinoma—results from a randomised phase II trial. Br. J Cancer 94, 218-226.

Echigo T, Hasegawa M, Shimada Y, Inaoki M, Takehara K, Sato S (2006). Both Th1 and Th2 chemokines are elevated in sera of patients with autoimmune blistering diseases. Arch. Dermatol. Res 298, 38-45.

Fujii H, Shimada Y, Hasegawa M, Takehara K, Sato S (2004). Serum levels of a Th1 chemoattractant IP-10 and Th2 chemoattractants, TARC and MDC, are elevated in patients with systemic sclerosis. J. Dermatol. Sci. 35, 43-51.

Haeryfar S M, Berczi I (2001). The thymus and the acute phase response. Cell Mol. Biol. (Noisy.-le-grand) 47, 145-156.

Leung T F, Ma K C, Hon K L, Lam C W, Wan H, Li C Y, Chan I H (2003). Serum concentration of macrophage-derived chemokine may be a useful inflammatory marker for assessing severity of atopic dermatitis in infants and young children. Pediatr. Allergy Immunol. 14, 296-301.

Moroni M, Porta C, De A M, Quaglini S, Cattabiani M A, Buzio C (2000). Eosinophils and C4 predict clinical failure of combination immunotherapy with very low dose subcutaneous interleukin-2 and interferon in renal cell carcinoma patients. Haematologica 85, 298-303.

Muller A J, Sharma M D, Chandler P R, Duhadaway J B, Everhart M E, Johnson B A, III, Kahler D J, Pihkala J, Soler A P, Munn D H, Prendergast G C, Mellor A L (2008). Chronic inflammation that facilitates tumor progression creates local immune suppression by inducing indoleamine 2,3 dioxygenase. Proc Natl. Acad. Sci. U.S.A 105, 17073-17078.

Panse J, Friedrichs K, Marx A, Hildebrandt Y, Luetkens T, Barrels K, Horn C, Stahl T, Cao Y, Milde-Langosch K, Niendorf A, Kroger N, Wenzel S, Leuwer R, Bokemeyer C, Hegewisch-Becker S, Atanackovic D (2008). Chemokine CXCL13 is overexpressed in the tumour tissue and in the peripheral blood of breast cancer patients. Br. J Cancer 99, 930-938.

Rashid F, Waraich N, Bhatti I, Saha S, Khan R N, Ahmed J, Leeder P C, Larvin M, Iftikhar S Y (2010). A pre-operative elevated neutrophil: lymphocyte ratio does not predict survival from oesophageal cancer resection. World J Surg Oncol 8, 1.

Riesen, W F (2008). Fettstoffwechsel, Referenzbereich. In Labor and Diagnose, L. Thomas, ed. (Frankfurt/Main: TH-Books Verlagsgesellschaft mbH), p. 236.

Saeki H, Tamaki K (2006). Thymus and activation regulated chemokine (TARC)/CCL17 and skin diseases. J. Dermatol. Sci. 43, 75-84.

Sansonno D, Tucci F A, Troiani L, Lauletta G, Montrone M, Conteduca V, Sansonno L, Dammacco F (2008). Increased serum levels of the chemokine CXCL13 and up-regulation of its gene expression are distinctive features of HCV-related cryoglobulinemia and correlate with active cutaneous vasculitis. Blood 112, 1620-1627.

Sasaki A, Iwashita Y, Shibata K, Matsumoto T, Ohta M, Kitano S (2006). Prognostic value of preoperative peripheral blood monocyte count in patients with hepatocellular carcinoma. Surgery 139, 755-764.

Sekiya T, Yamada H, Yamaguchi M, Yamamoto K, Ishii A, Yoshie 0, Sano Y, Morita A, Matsushima K, Hirai K (2002). Increased levels of a TH2-type CC chemokine thymus and activation-regulated chemokine (TARC) in serum and induced sputum of asthmatics. Allergy 57, 173-177.

Shimada Y, Takehara K, Sato S (2004). Both Th2 and Th1 chemokines (TARC/CCL17, MDC/CCL22, and Mig/CXCL9) are elevated in sera from patients with atopic dermatitis. J. Dermatol. Sci. 34, 201-208.

Simon D, Simon HU (2007). Eosinophilic disorders. J Allergy Clin Immunol 119, 1291-1300.

Su F, Kozak K R, Imaizumi S, Gao F, Amneus M W, Grijalva V, Ng C, Wagner A, Hough G, Farias-Eisner G, Ananthara-maiah G M, Van Lenten B J, Navab M, Fogelman A M, Reddy S T, Farias-Eisner R (2010). Apolipoprotein A-I (apoA-I) and apoA-I mimetic peptides inhibit tumor development in a mouse model of ovarian cancer. Proc Natl. Acad. Sci. U.S.A.

Sugawara N, Yamashita T, Ote Y, Miura M, Terada N, Kuro-sawa M (2002). TARC in allergic disease. Allergy 57, 180-181.

Vallejo A N, Weyand C M, Goronzy J J (2004). T-cell senescence: a culprit of immune abnormalities in chronic inflammation and persistent infection. Trends Mol. Med 10, 119-124.

Vermaat J S, van dT, I, Mehra N, Sleijfer S, Haanen J B, Roodhart J M, Engwegen J Y, Korse C M, Langenberg M H, Kruit W, Groenewegen G, Giles R H, Schellens J H, Beijnen J H, Voest E E (2010). Two-protein signature of novel serological markers apolipoprotein-A2 and serum amyloid alpha predicts prognosis in patients with metastatic renal cell cancer and improves the currently used prognostic survival models. Ann Oncol 21, 1472-1481.

Wanner, C., P. Schollmeyer, and W. H. Horl. 1988. Serum carnitine levels and carnitine esters of patients after kidney transplantation: role of immunosuppression. Metabolism 37:263-267.

Longenecker, B. M., M. Reddish, R. Koganty, and G. D. MacLean. 1993 Immune responses of mice and human breast cancer patients following immunization with synthetic sialyl-Tn conjugated to KLH plus detox adjuvant. Ann N.Y. Acad. Sci. 690:276-291.

Sachan, D. S. and W. L. Dodson. 1987. The serum carnitine status of cancer patients. J Am Coll. Nutr. 6:145-150.

Banchereau, J., A. K. Palucka, M. Dhodapkar, S. Burkeholder, N. Taquet, A. Rolland, S. Taquet, S. Coquery, K. M. Wittkowski, N. Bhardwaj, L. Pineiro, R. Steinman, and J. Fay. 2001a. Immune and clinical responses in patients with metastatic melanoma to CD34(+) progenitor-derived dendritic cell vaccine. Cancer Res. 61:6451-6458.

The invention claimed is:

1. A method for predicting whether an immunotherapy will have a beneficial effect in a cancer patient, comprising
   a) determining a level of CCL17/TARC (chemokine C-C motif ligand 17/thymus and activation regulated chemokine) in a sample from said cancer patient, wherein a level of said marker at least 10% higher as compared to a median level of said marker in a given cancer patient population is indicative of a beneficial effect of an immunotherapy for said cancer patient, wherein said cancer patient is experiencing a cancer selected from the group consisting of renal cell carcinoma (RCC), colorectal cancer (CRC), gastric cancer (GC), melanoma, non-small-cell lung cancer (NSCLC), glioblastoma, and adenocarcinomas of any type;
   and, optionally,
   b) determining a level of at least one marker selected from the group consisting of B-cell attracting chemokine (CXCL13/BCA-1), neutrophils, interleukin-6 (IL-6), and short-chain acylcarnitines in a sample from said cancer patient, wherein a level of said marker at least 10% lower compared to a median level of said marker in a given cancer patient population is indicative of a beneficial effect of an immunotherapy for said patient,
   wherein said sample is selected from the group consisting of whole blood, peripheral blood, or fractions thereof, serum, buffy coat, tumor tissue, lymphatic fluid, urine, bone marrow, EDTA plasma, heparinized plasma, citrate plasma, heparinized whole blood, and frozen samples thereof, including frozen heparinized whole blood;
   wherein said determining comprises at least one method selected from the group consisting of immunoassays, bead-based immunoassays, multiplex immunoassays, ELISA, microarray based assays, epigenetic assays, expression analysis, FACS analysis, established methods of hematology, proteomics, and mass spectrometry;
   wherein said immunotherapy comprises vaccination with an anti-cancer vaccine, optionally together with an adjuvant, which optionally comprises GM-CSF, wherein said vaccination is at least one vaccine comprising at least one immunogenic peptide selected from the group of SEQ ID NO: 1 to 37; and
   wherein said beneficial effect is selected from the group consisting of longer overall survival, occurrence of single and/or multiple T-cell responses induced by the immunotherapy, retardation of tumor growth, tumor shrinkage, and longer progression-free survival.

2. The method according to claim 1, further comprising
   c) determining a level of at least one marker selected from the group consisting of albumin, and direct bilirubin in said sample from said patient, wherein a level of said marker at least 10% higher compared to a median level of said marker in a given cancer patient population is indicative of a beneficial effect of the immunotherapy for said patient,
   and, optionally,
   d) determining a level of a marker comprising interleukin-33 (IL-33) in said sample from said patient, wherein a level of said marker at least 10% lower compared to the median level of said marker in a given cancer patient population is indicative of a beneficial effect of the immunotherapy for said patient.

3. The method according to claim 1, wherein said patient is treated or has been pre-treated with one or more therapies comprising surgery, radiotherapy and/or chemotherapy, and optionally one or more therapies wherein said patient is treated or has been pre-treated with an anti-cancer agent selected from the group consisting of cytokines, and tyrosine kinase inhibitors (TKI), optionally comprising sorafenib and sunitinib, and cyclophosphamide.

4. The method according to claim 1, further comprising prognosing the effect of said immunotherapy in said patient.

5. The method according to claim 1, further comprising monitoring an effect of said immunotherapy in said patient, comprising conducting at least two of said determining (a) and/or (b) steps.

6. The method of claim 1, wherein at least one peptide is selected from the group consisting of SEQ ID NO: 1 to 10.

7. The method of claim 1, wherein at least one peptide is selected from the group consisting of SEQ ID NO: 1, 5, 8, 9, and 11-19.

8. The method of claim 1, wherein at least one peptide is selected from the group consisting of SEQ ID NO: 20-29.

9. The method of claim 1, wherein at least one peptide is selected from the group consisting of SEQ ID NO: 30-37.

* * * * *

SEQUENCE LISTING

<160> NUMBER OF SEQ ID NOS: 50

<210> SEQ ID NO 1
<211> LENGTH: 16
<212> TYPE: PRT
<213> ORGANISM: Homo sapiens

<400> SEQUENCE: 1

Ser Gln Asp Asp Ile Lys Gly Ile Gln Lys Leu Tyr Gly Lys Arg Ser
1               5                   10                  15

<210> SEQ ID NO 2
<211> LENGTH: 9
<212> TYPE: PRT
<213> ORGANISM: Homo sapiens

<400> SEQUENCE: 2

Val Met Ala Gly Asp Ile Tyr Ser Val
1               5

<210> SEQ ID NO 3
<211> LENGTH: 9
<212> TYPE: PRT
<213> ORGANISM: Homo sapiens

<400> SEQUENCE: 3

Ser Val Ala Ser Thr Ile Thr Gly Val
1               5

<210> SEQ ID NO 4
<211> LENGTH: 9
<212> TYPE: PRT
<213> ORGANISM: Homo sapiens

<400> SEQUENCE: 4

Ala Leu Ala Asp Gly Val Gln Lys Val
1               5

<210> SEQ ID NO 5
<211> LENGTH: 9
<212> TYPE: PRT
<213> ORGANISM: Homo sapiens

<400> SEQUENCE: 5

Leu Leu Gly Ala Thr Cys Met Phe Val
1               5

<210> SEQ ID NO 6
<211> LENGTH: 9
<212> TYPE: PRT
<213> ORGANISM: Homo sapiens

<400> SEQUENCE: 6

Ser Val Phe Ala Gly Val Val Gly Val
1               5

<210> SEQ ID NO 7
<211> LENGTH: 9
<212> TYPE: PRT
<213> ORGANISM: Homo sapiens

<400> SEQUENCE: 7

Ala Leu Phe Asp Gly Asp Pro His Leu
1               5

```
<210> SEQ ID NO 8
<211> LENGTH: 9
<212> TYPE: PRT
<213> ORGANISM: Homo sapiens

<400> SEQUENCE: 8

Tyr Val Asp Pro Val Ile Thr Ser Ile
1               5

<210> SEQ ID NO 9
<211> LENGTH: 9
<212> TYPE: PRT
<213> ORGANISM: Homo sapiens

<400> SEQUENCE: 9

Ser Thr Ala Pro Pro Val His Asn Val
1               5

<210> SEQ ID NO 10
<211> LENGTH: 9
<212> TYPE: PRT
<213> ORGANISM: Homo sapiens

<400> SEQUENCE: 10

Leu Ala Ala Leu Pro His Ser Cys Leu
1               5

<210> SEQ ID NO 11
<211> LENGTH: 9
<212> TYPE: PRT
<213> ORGANISM: Homo sapiens

<400> SEQUENCE: 11

Ala Leu Ser Asn Leu Glu Val Thr Leu
1               5

<210> SEQ ID NO 12
<211> LENGTH: 9
<212> TYPE: PRT
<213> ORGANISM: Homo sapiens

<400> SEQUENCE: 12

Ile Leu Ala Pro Val Ile Leu Tyr Ile
1               5

<210> SEQ ID NO 13
<211> LENGTH: 9
<212> TYPE: PRT
<213> ORGANISM: Homo sapiens

<400> SEQUENCE: 13

Ile Leu Asp Gln Lys Ile Asn Glu Val
1               5

<210> SEQ ID NO 14
<211> LENGTH: 10
<212> TYPE: PRT
<213> ORGANISM: Homo sapiens

<400> SEQUENCE: 14

Lys Leu Met Asp Leu Asp Val Glu Gln Leu
1               5                   10

<210> SEQ ID NO 15
```

-continued

```
<211> LENGTH: 10
<212> TYPE: PRT
<213> ORGANISM: Homo sapiens

<400> SEQUENCE: 15

Ala Leu Phe Val Arg Leu Leu Ala Leu Ala
1               5                   10

<210> SEQ ID NO 16
<211> LENGTH: 10
<212> TYPE: PRT
<213> ORGANISM: Homo sapiens

<400> SEQUENCE: 16

Lys Ile Phe Asp Glu Ile Leu Val Asn Ala
1               5                   10

<210> SEQ ID NO 17
<211> LENGTH: 15
<212> TYPE: PRT
<213> ORGANISM: Homo sapiens

<400> SEQUENCE: 17

Thr Pro Pro Ile Asp Ala His Thr Arg Asn Leu Leu Arg Asn His
1               5                   10                  15

<210> SEQ ID NO 18
<211> LENGTH: 16
<212> TYPE: PRT
<213> ORGANISM: Homo sapiens

<400> SEQUENCE: 18

Ser Pro Gln Tyr Ser Trp Arg Ile Asn Gly Ile Pro Gln Gln His Thr
1               5                   10                  15

<210> SEQ ID NO 19
<211> LENGTH: 9
<212> TYPE: PRT
<213> ORGANISM: Homo sapiens

<400> SEQUENCE: 19

Tyr Leu Ser Gly Ala Asn Leu Asn Leu
1               5

<210> SEQ ID NO 20
<211> LENGTH: 10
<212> TYPE: PRT
<213> ORGANISM: Homo sapiens

<400> SEQUENCE: 20

Leu Tyr Gln Ile Leu Gln Gly Ile Val Phe
1               5                   10

<210> SEQ ID NO 21
<211> LENGTH: 9
<212> TYPE: PRT
<213> ORGANISM: Homo sapiens

<400> SEQUENCE: 21

Ser Tyr Asn Pro Leu Trp Leu Arg Ile
1               5

<210> SEQ ID NO 22
<211> LENGTH: 9
<212> TYPE: PRT
```

```
<213> ORGANISM: Homo sapiens

<400> SEQUENCE: 22

Asn Tyr Leu Pro Phe Ile Met Glu Leu
1               5

<210> SEQ ID NO 23
<211> LENGTH: 9
<212> TYPE: PRT
<213> ORGANISM: Homo sapiens

<400> SEQUENCE: 23

Ser Tyr Ile Asp Val Leu Pro Glu Phe
1               5

<210> SEQ ID NO 24
<211> LENGTH: 9
<212> TYPE: PRT
<213> ORGANISM: Homo sapiens

<400> SEQUENCE: 24

Ser Tyr Ile Ile Asp Pro Leu Asn Leu
1               5

<210> SEQ ID NO 25
<211> LENGTH: 10
<212> TYPE: PRT
<213> ORGANISM: Homo sapiens

<400> SEQUENCE: 25

Tyr Tyr Asn Ala Ala Gly Phe Asn Lys Leu
1               5                   10

<210> SEQ ID NO 26
<211> LENGTH: 9
<212> TYPE: PRT
<213> ORGANISM: Homo sapiens

<400> SEQUENCE: 26

Asn Tyr Leu Leu Tyr Val Ser Asn Phe
1               5

<210> SEQ ID NO 27
<211> LENGTH: 9
<212> TYPE: PRT
<213> ORGANISM: Homo sapiens

<400> SEQUENCE: 27

Ala Tyr Leu Val Tyr Thr Asp Arg Leu
1               5

<210> SEQ ID NO 28
<211> LENGTH: 9
<212> TYPE: PRT
<213> ORGANISM: Homo sapiens

<400> SEQUENCE: 28

His Tyr Lys Pro Thr Pro Leu Tyr Phe
1               5

<210> SEQ ID NO 29
<211> LENGTH: 10
<212> TYPE: PRT
<213> ORGANISM: Homo sapiens
```

```
<400> SEQUENCE: 29

Val Trp Ser Asp Val Thr Pro Leu Thr Phe
1               5                   10

<210> SEQ ID NO 30
<211> LENGTH: 9
<212> TYPE: PRT
<213> ORGANISM: Homo sapiens

<400> SEQUENCE: 30

Thr Met Leu Ala Arg Leu Ala Ser Ala
1               5

<210> SEQ ID NO 31
<211> LENGTH: 9
<212> TYPE: PRT
<213> ORGANISM: Homo sapiens

<400> SEQUENCE: 31

Leu Thr Phe Gly Asp Val Val Ala Val
1               5

<210> SEQ ID NO 32
<211> LENGTH: 9
<212> TYPE: PRT
<213> ORGANISM: Homo sapiens

<400> SEQUENCE: 32

Asn Leu Asp Thr Leu Met Thr Tyr Val
1               5

<210> SEQ ID NO 33
<211> LENGTH: 9
<212> TYPE: PRT
<213> ORGANISM: Homo sapiens

<400> SEQUENCE: 33

Ala Met Thr Gln Leu Leu Ala Gly Val
1               5

<210> SEQ ID NO 34
<211> LENGTH: 9
<212> TYPE: PRT
<213> ORGANISM: Homo sapiens

<400> SEQUENCE: 34

Gly Leu Trp His His Gln Thr Glu Val
1               5

<210> SEQ ID NO 35
<211> LENGTH: 9
<212> TYPE: PRT
<213> ORGANISM: Homo sapiens

<400> SEQUENCE: 35

Lys Ile Gln Glu Ile Leu Thr Gln Val
1               5

<210> SEQ ID NO 36
<211> LENGTH: 9
<212> TYPE: PRT
<213> ORGANISM: Homo sapiens
```

```
<400> SEQUENCE: 36

Ala Leu Trp Ala Trp Pro Ser Glu Leu
1               5

<210> SEQ ID NO 37
<211> LENGTH: 17
<212> TYPE: PRT
<213> ORGANISM: Homo sapiens

<400> SEQUENCE: 37

Thr Phe Ser Tyr Val Asp Pro Val Ile Thr Ser Ile Ser Pro Lys Tyr
1               5                   10                  15

Gly

<210> SEQ ID NO 38
<211> LENGTH: 10
<212> TYPE: PRT
<213> ORGANISM: Homo sapiens

<400> SEQUENCE: 38

Phe Leu Thr Pro Lys Lys Leu Gln Cys Val
1               5                   10

<210> SEQ ID NO 39
<211> LENGTH: 9
<212> TYPE: PRT
<213> ORGANISM: Homo sapiens

<400> SEQUENCE: 39

Lys Leu Gln Cys Val Asp Leu His Val
1               5

<210> SEQ ID NO 40
<211> LENGTH: 10
<212> TYPE: PRT
<213> ORGANISM: Homo sapiens

<400> SEQUENCE: 40

Val Ile Ser Asn Asp Val Cys Ala Gln Val
1               5                   10

<210> SEQ ID NO 41
<211> LENGTH: 9
<212> TYPE: PRT
<213> ORGANISM: Homo sapiens

<400> SEQUENCE: 41

Ala Leu Gln Pro Gly Thr Ala Leu Leu
1               5

<210> SEQ ID NO 42
<211> LENGTH: 9
<212> TYPE: PRT
<213> ORGANISM: Homo sapiens

<400> SEQUENCE: 42

Ala Ile Leu Ala Leu Leu Pro Ala Leu
1               5

<210> SEQ ID NO 43
<211> LENGTH: 9
<212> TYPE: PRT
<213> ORGANISM: Homo sapiens
```

```
<400> SEQUENCE: 43

Leu Leu His Glu Thr Asp Ser Ala Val
1               5

<210> SEQ ID NO 44
<211> LENGTH: 9
<212> TYPE: PRT
<213> ORGANISM: Homo sapiens

<400> SEQUENCE: 44

Ala Leu Phe Asp Ile Glu Ser Lys Val
1               5

<210> SEQ ID NO 45
<211> LENGTH: 10
<212> TYPE: PRT
<213> ORGANISM: Homo sapiens

<400> SEQUENCE: 45

Glu Leu Thr Leu Gly Glu Phe Leu Lys Leu
1               5                   10

<210> SEQ ID NO 46
<211> LENGTH: 10
<212> TYPE: PRT
<213> ORGANISM: Homo sapiens

<400> SEQUENCE: 46

Thr Leu Pro Pro Ala Trp Gln Pro Phe Leu
1               5                   10

<210> SEQ ID NO 47
<211> LENGTH: 9
<212> TYPE: PRT
<213> ORGANISM: Homo sapiens

<400> SEQUENCE: 47

Gly Leu Met Lys Tyr Ile Gly Glu Val
1               5

<210> SEQ ID NO 48
<211> LENGTH: 9
<212> TYPE: PRT
<213> ORGANISM: Homo sapiens

<400> SEQUENCE: 48

Cys Leu Ala Ala Gly Ile Thr Tyr Val
1               5

<210> SEQ ID NO 49
<211> LENGTH: 15
<212> TYPE: PRT
<213> ORGANISM: Homo sapiens

<400> SEQUENCE: 49

Asn Tyr Thr Leu Arg Val Asp Cys Thr Pro Leu Met Tyr Ser Leu
1               5                   10                  15

<210> SEQ ID NO 50
<211> LENGTH: 15
<212> TYPE: PRT
<213> ORGANISM: Homo sapiens
```

```
<400> SEQUENCE: 50

Thr Leu Gly Glu Phe Leu Lys Leu Asp Arg Glu Arg Ala Lys Asn
1               5                   10                  15
```